United States Patent
Gelbin et al.

(10) Patent No.: US 8,008,384 B2
(45) Date of Patent: Aug. 30, 2011

(54) LIQUID BUTYLARYL PHOSPHITE COMPOSITIONS

(75) Inventors: Michael E. Gelbin, Middlebury, CT (US); Maurice Power, Manchester (GB); Jonathan S. Hill, Manchester (GB)

(73) Assignee: Chemtura Corporation, Middlebury, CT (US)

( * ) Notice: Subject to any disclaimer, the term of this patent is extended or adjusted under 35 U.S.C. 154(b) by 0 days.

(21) Appl. No.: 12/534,010

(22) Filed: Jul. 31, 2009

(65) Prior Publication Data

US 2010/0190900 A1   Jul. 29, 2010

Related U.S. Application Data

(63) Continuation-in-part of application No. 11/787,531, filed on Apr. 16, 2007.

(60) Provisional application No. 60/815,819, filed on Jun. 20, 2006.

(51) Int. Cl.
C08K 5/52 (2006.01)

(52) U.S. Cl. ....................................... 524/128

(58) Field of Classification Search .................. 524/128
See application file for complete search history.

(56) References Cited

U.S. PATENT DOCUMENTS

| | | | |
|---|---|---|---|
| 2,220,845 A | 11/1940 | Moyle | |
| 2,834,798 A | 5/1958 | Hechenbleikner et al. | |
| 3,412,064 A | 11/1968 | Brindell | |
| 3,492,377 A | 1/1970 | Kline | |
| 3,558,554 A | 1/1971 | Kuriyama et al. | |
| 3,644,536 A | 2/1972 | Bafford | |
| 3,755,200 A | 8/1973 | Rhodes et al. | |
| 3,756,906 A | 9/1973 | Nicholas et al. | |
| 3,787,537 A | 1/1974 | De Marcq | |
| 4,261,880 A | 4/1981 | Fujii et al. | |
| 4,276,233 A | 6/1981 | Markezich et al. | |
| 4,321,218 A | 3/1982 | Rasberger | |
| 4,383,950 A | 5/1983 | Rasberger | |
| 4,406,842 A | 9/1983 | Spivack | |
| 4,492,661 A | 1/1985 | Maul et al. | |
| 4,829,112 A | 5/1989 | Ishii et al. | |
| 5,208,368 A | 5/1993 | Scherzer et al. | |
| 5,254,610 A | 10/1993 | Small, Jr. et al. | |
| 5,254,709 A | 10/1993 | Hunter | |
| 5,322,871 A | 6/1994 | Pitteloud et al. | |
| 5,401,845 A | 3/1995 | Pitteloud et al. | |
| 5,532,401 A | 7/1996 | Stevenson et al. | |
| 5,561,181 A | 10/1996 | Mahood | |
| 6,576,788 B1 | 6/2003 | Penzel et al. | |
| 6,824,711 B2 | 11/2004 | Stevenson et al. | |
| 6,846,859 B2 | 1/2005 | Coffy et al. | |
| 6,887,926 B1 | 5/2005 | Parhar et al. | |
| 7,157,511 B2 | 1/2007 | Bobsein et al. | |
| 7,176,252 B2 | 2/2007 | Stevenson et al. | |
| 7,320,764 B2 | 1/2008 | Stevenson et al. | |
| 7,361,703 B2 | 4/2008 | Tikuisis et al. | |
| 7,468,410 B2 | 12/2008 | Chafin et al. | |
| 2003/0078340 A1 | 4/2003 | Fatnes et al. | |
| 2004/0048958 A1 | 3/2004 | Didier | |
| 2007/0149660 A1 | 6/2007 | Kumar et al. | |
| 2007/0228343 A1 | 10/2007 | Roth et al. | |

FOREIGN PATENT DOCUMENTS

| | | |
|---|---|---|
| CZ | 8901540 | 1/1993 |
| DE | 2940620 | 4/1981 |
| EP | 0 090 524 | 10/1983 |
| EP | 0 245 852 | 11/1987 |
| EP | 0551 062 | 7/1993 |
| GB | 1 298 248 | 11/1972 |
| GB | 2 227 490 | 8/1990 |
| JO | JP5202236 | 8/1993 |
| JP | 59030842 | 2/1984 |
| JP | 7 309884 | 11/1995 |
| RO | 112871 | 1/1998 |
| RU | 2 140 938 | 11/1999 |
| WO | WO 2007/009916 A1 | 1/2007 |
| WO | 2007/149143 | 12/2007 |

OTHER PUBLICATIONS

International Preliminary Report on Patentability mailed Dec. 22, 2008; of PCT Application No. PCT/US2007/009690; 6 pgs.

DOVER Chemical Company—Data Sheet "Doverphos Liquid Phosphites" (2011).

*Primary Examiner* — David W Wu

*Assistant Examiner* — Sonya Wright

(74) *Attorney, Agent, or Firm* — Joseph Suhadolnik

(57) ABSTRACT

A phosphite composition comprising at least two of a tris(dibutylaryl) phosphite, a tris(monobutylaryl) phosphite, a bis(dibutylaryl)monobutylaryl phosphite, and a bis(monobutylaryl)dibutylaryl phosphite. The inventive phosphite composition is a liquid at ambient conditions.

20 Claims, No Drawings

LIQUID BUTYLARYL PHOSPHITE COMPOSITIONS

CROSS REFERENCE TO RELATED APPLICATION(S)

This application is a continuation-in-part of U.S. patent application Ser. No. 11/787,531, filed Apr. 16, 2007, which claims priority to U.S. Provisional Application No. 60/815,819, filed Jun. 20, 2006. Each of these applications is incorporated herein by reference in its entirety.

FIELD OF INVENTION

The present invention relates to novel compositions of phosphite antioxidants, which are useful, for example, in stabilizing polymeric compositions. More specifically, the invention relates to novel compositions of butylaryl phosphites that are liquid at ambient conditions and to stabilized polyolefin resin compositions and stabilizer concentrates comprising these novel liquid compositions of phosphites.

BACKGROUND OF THE INVENTION

Stabilizers are often used in polymeric compositions, e.g., polyolefins, polyvinyl halides, polyesters, polyamides, nitrile polymers, styrenic polymers and acrylate polymers and elastomeric materials such as butadiene rubber, polyisoprene etc to stabilize the polymeric compositions against the effects of heat and light degradation. Exemplary of such stabilizers are phenolic antioxidants, hindered amine light stabilizers, ultraviolet light absorbers, phosphite antioxidants, metal salts of fatty acids, hydrotalcites, metal oxides, epoxidized oils, hydroxylamines, amine oxides, lactones, and thiosynergists. In particular, organic phosphites have been used as antioxidants, e.g., secondary antioxidants, for polyolefins, polyvinyl chloride, and elastomers. Examples of such phosphites are disclosed in H. Zweifel (Ed) *Plastics Additives Handbook*, 5th edition, Hanser Publishers, Munich 2000. Phosphite stabilizers, both liquid and solid, are known in the art. Many of the most effective organic phosphites are solids at ambient temperature and, accordingly, do not lend themselves to being readily combined with certain polymeric resins. As such, these organic phosphites must be processed, e.g., heated or melted, in order to be incorporated into the respective polymer compositions. Alternatively, a solid phosphite may be mixed with a liquid phosphite to thus make a liquid composition. One of the most widely used solid organic phosphites is tris(2,4-di-t-butylphenyl) phosphite, which is commercially sold under the trade names Alkanox™ 240 (Chemtura Corporation, Middlebury, Conn., USA), Irgafos™ 168 (Ciba Specialty Chemicals Corporation, Tarrytown, N.Y., USA), or Doverphos™ S-480 (Dover Chemical Corp, Dover, Ohio, USA). Tris(2,4-di-t-butylphenyl)phosphite has processability and solubility limitations, however, due to its solid form. Examples of other solid phosphites include bis(2,4-di-tert-butylphenyl)pentaerythritol diphosphite, which is commerical sold under the trade name Ultranox™ 626 (Chemtura Corporation, Middlebury, Conn., USA).

Liquid phosphite antioxidants typically do not have the processability and solubility concerns that are associated with solid phosphites. There are several different liquid phosphites, including tris(nonylphenyl)phosphite (TNPP), bis(decyl) pentaerythritol diphosphite, tris(dipropyleneglycol)phosphite, 4,4'-isopropylidenebis(didodecyl phenyl phosphite), dilaurylphenylphosphite and trilaurylphosphite (TLP). However, TNPP is widely used with most polymeric resins, especially polyolefins. Due to alleged estrogenicity concerns associated with nonylphenol, which may be present in low concentrations in some commercially available TNPP products, there is a strong desire in the art to replace TNPP with other liquid phosphites that are effective stabilizers, but which do not present such estrogenicity concerns.

Thus, the need exists for safe and effective phosphite stabilizers, that can effectively stabilize polymer resins and compositions against heat and light degradation and that are liquids at ambient conditions.

SUMMARY OF THE INVENTION

The present invention, in one embodiment, is directed to a butylaryl phosphite composition that is liquid at ambient conditions. In one embodiment, the inventive phosphite composition comprises at least two of a tris(dibutylaryl) phosphite, a tris(monobutylaryl) phosphite, a bis(dibutylaryl) monobutylaryl phosphite, and a bis(monobutylaryl) dibutylaryl phosphite. In another embodiment, the composition comprises tris(monobutylaryl) phosphite in an amount ranging from 20 to 70 weight percent and bis(monobutylaryl)dibutylaryl phosphite in an amount ranging from 15 to 60 weight percent. Preferably, the butyl groups on the butylaryl substituents are tert-butyl groups. This inventive composition is a liquid capable of completing three freeze/thaw cycles without solidification and/or crystallization.

In another embodiment, the invention relates to a method for preparing the above-mentioned liquid phosphite composition. The inventive method comprises reacting a phosphorus polyhalide with a composition of alkylated phenols to produce the liquid phosphite composition. In preferred embodiments, the composition of alkylated phenols comprises monobutylated phenols and dibutylated phenols and is selected and/or adjusted so as to produce the desired resultant phosphite composition. In other embodiments, the method includes the step of removing unreacted phenols from a crude phosphite composition to form the resultant phosphite composition. In doing so, the resultant phosphite composition may be substantially free of phenols.

In another embodiment, the invention relates to a process for stabilizing a polymeric composition, which comprises adding to the polymeric composition and effective amount of the above-mentioned liquid phosphite composition. Thus, the invention further relates to a stabilized polymeric composition comprising the above-mentioned liquid phosphite composition and a polymeric resin. This polymeric composition demonstrates improved properties and characteristics, e.g., the polymeric compositions are effectively stabilized against oxidative degradation.

DETAILED DESCRIPTION OF THE INVENTION

Introduction

The present invention relates to the stabilization of polymeric compositions with liquid phosphite compositions and specifically butylaryl phosphite compositions. In a preferred embodiment, the liquid phosphite composition comprises at least two of a tris(dibutylaryl) phosphite, a tris(monobutylaryl) phosphite, a bis(dibutylaryl)monobutylaryl phosphite, and a bis(monobutylaryl)dibutylaryl phosphite. The invention also relates to processes for forming such liquid phosphite compositions, to polymeric compositions incorporating such compositions, and to processes for stabilizing polymeric compositions with such compositions.

By incorporating such liquid phosphite compositions, i.e., butylaryl phosphite compositions, into polymeric compositions, the characteristics and/or properties of the polymeric composition, for example, color, e.g., as measured by yellowing index, melt flow index, and oxygen induction time, may be significantly improved. In addition, unlike solid phosphite compositions, the inventive liquid phosphite compositions beneficially may be incorporated into polymeric compositions without melting. Further, the phosphite compositions of the invention are not believed to present any health or safety concerns.

Phosphite Compositions

In one embodiment, the present invention relates to a phosphite composition comprising at least two different phosphites of structure (I):

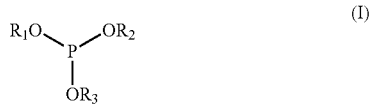

wherein $R_1$, $R_2$, and $R_3$ are independently selected butylaryl groups and wherein the composition is a liquid at ambient conditions. By "ambient conditions," it is meant room temperature, e.g., 25° C., and about 1 atmosphere pressure.

In one embodiment, the aryl moiety present in the compounds of the present invention is an aromatic moiety of from 6 to 18 carbon atoms, e.g., phenyl, naphthyl, phenanthryl, anthracyl, biphenyl, terphenyl, o-cresyl, m-cresyl, p-cresyl, and the like, preferably phenyl.

Since the phosphite composition comprises at least two butylaryl phosphite compounds, for at least some of the phosphite compounds in the phosphite composition, the aryl moiety is substituted with one or more butyl groups, i.e., any $C_4$-containing species.

In the butylaryl phosphite compounds, the aromatic moieties may be mono, di or tri substituted in one or more of the ortho-, meta- and/or para-positions, typically one or more of the ortho- and/or para-positions, with a butyl group.

As indicated above, the phosphite composition comprises at least two different phosphites, e.g., at least three different phosphites, or at least four different phosphites, selected from the group consisting of a tris(dibutylaryl)phosphite, a tris(monobutylaryl) phosphite, a bis(dibutylaryl)monobutylaryl phosphite, and a bis(monobutylaryl)dibutylaryl phosphite. Thus, the phosphite composition comprises at least one phosphite that has at least one aromatic moiety that is multiply substituted, such as a bis(dibutylaryl)monobutylaryl phosphite, a bis(monobutylaryl)dibutylaryl phosphite or a tris(dibutylaryl) phosphite. That is, the phosphite composition does not contain exclusively monosubstituted butylaryl phosphite compounds. In addition to containing multiply-substituted butylaryl phosphite compounds, however, the phosphite composition preferably includes at least one phosphite compound in which each aryl moiety is monosubstituted, e.g., a tris(monobutylaryl) phosphite.

Alkyl Substituents

As indicated above, the aryl moieties in at least some of the phosphite compounds in the phosphite composition are substituted with one or more butyl groups, i.e., any $C_4$-containing species, such as, for example, n-butyl, tert-butyl, sec-butyl, iso-butyl, etc.

In some embodiments, the phosphite composition comprises phosphite compounds that are exclusively alkylated with butyl substituents—the phosphite composition does not contain any phosphites that contain aryl moieties that are substituted with non-butyl groups.

In other embodiments, however, the phosphite composition may comprise one or more non-butylaryl phosphite compounds in addition to the butylaryl phosphite compounds. By non-butylaryl phosphite compound it is meant any alkylaryl phosphite compound in which at least one of the aryl moieties is unsubstituted or is substituted with an alkyl group other than butyl. If the phosphite composition comprises any non-butylaryl phosphite compounds, then the non-butyl substitutent may comprise, for example, one or more $C_1$-$C_{18}$ alkyl groups other than butyl, e.g., $C_5$-$C_{10}$ alkyl groups. In this aspect, the non-butyl alkyl substituent(s) on the aryl moieties may be selected from straight-chain or branched $C_1$-$C_{18}$ alkyl, e.g., $C_1$-$C_{10}$ alkyl, $C_1$-$C_8$ alkyl, $C_5$-$C_{10}$ alkyl, $C_5$-$C_6$ alkyl or $C_5$ alkyl ("amyl" groups), other than butyl. The one or more non-butyl alkyl substituent may include, for example, methyl, ethyl, propyl, amyl (especially sec-amyl, iso-amyl, and/or tert-amyl), hexyl, heptyl, octyl, nonyl (although less preferred), decyl, undecyl, dodecyl, tridecyl, tetradecyl, pentadecyl, hexadecyl, heptadecyl, octadecyl, and isomers thereof. As a preferred example, the phosphite composition, in addition to the butyl substituent(s), contains propyl, amyl, dodecyl, and/or $C_5$-$C_{10}$ substituents.

In a preferred embodiment, the phosphite composition is substantially free of $C_8$-$C_{10}$ alkyl groups. In preferred embodiments, the alkyl moieties do not include nonyl, meaning the phosphite composition preferably comprises less than 50 wppm, e.g., less than 10 wppm or less than 5 wppm nonyl substituted aryl phosphite compounds, and most preferably no detectable nonyl substituted aryl phosphite compounds. In addition, the phosphite composition is substantially free of nonyl/aryl preferably comprises less than 50 wppm, e.g., less than 10 wppm or less than 5 wppm nonylphenol, and most preferably no detectable nonylphenol. The term "wppm" refers to parts per million based on the total weight of the phosphite composition.

In one embodiment, substantially all of the phosphite compounds in the phosphite composition, e.g., at least 90 wt. %, at least 95 wt. %, or at least 99 wt. % of the phosphite compounds in the phosphite composition, are butylaryl phosphite compounds. As such, the aryl moieties of the phosphite (s) are butyl-substituted aryl groups (butylaryl groups). As indicated above, the butyl groups may be straight chain butyl groups and/or branched butyl groups. Examples of preferred butyl groups include sec-butyl, iso-butyl, and tert-butyl. In a preferred embodiment, at least 90%, e.g., at least 95%, at least 98%, or at least 99% of the aryl moieties are substituted with one or more tert-butyl groups. Similarly, in a preferred embodiment, at least 90%, e.g., at least 95%, at least 98%, or at least 99% of the butyl substitutuents are tert-butyl substituents.

Butylaryl Moieties

As indicated above, in some embodiments, the alkylaryl moiety present in the compounds of the present invention is an aromatic moiety of from 6 to 18 carbon atoms, e.g., phenyl, naphthyl, phenanthryl, anthracyl, biphenyl, terphenyl, o-cresyl, m-cresyl, p-cresyl, xylyl (for example, 3,4-xylyl, 3,5-xylyl, or 2,6-xylyl) and the like, preferably phenyl. In one embodiment, each aromatic moiety is substituted with at least one, e.g., at least two or at least three butyl groups, as discussed above. Preferably, a first portion of the aryl moieties are mono-butyl substituted, and a second portion of the aryl moieties are di-butyl substituted.

As an example, where the aryl moiety is phenyl, the monobutylated aryl group may correspond to any of the structures (II)-(IV):

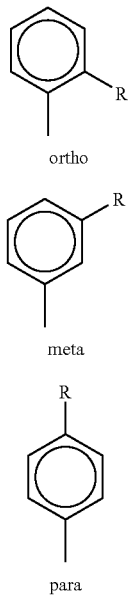

ortho (II)

meta (III)

para (IV)

wherein R is a butyl group, e.g., n-butyl, t-butyl, iso-butyl or sec-butyl, preferably tert-butyl.

Similarly, where the aryl moiety is phenyl, the dibutylaryl group may correspond to the structure:

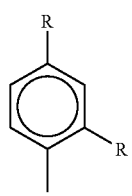

(V)

wherein R is a butyl group, e.g., n-butyl, tert-butyl, iso-butyl or sec-butyl. The two butyl groups may be of the same type or different from one another. For example, both butyl groups may be t-butyl, or one butyl group may be t-butyl and the other butyl group may be sec-butyl. In addition to the dibutylaryl groups of structure (V), the dibutylaryl groups may be 2,5-, 2,6-, and/or 3,5-substituted.

The phosphite composition may comprise phosphite compounds having at least one tributylaryl group, e.g., an aryl group that is substituted with three butyl groups, the same or different, e.g., n-butyl, tert-butyl, iso-butyl or sec-butyl. For example, where the aryl moiety is phenyl, the tributylaryl group may be substituted in the two ortho positions and in the para position. In addition, it is also contemplated that the phenyl group is 2,4,5-substituted.

The butyl groups may be substituted at any position on the aromatic moiety. In embodiments wherein the aryl moiety is a mono-substituted phenyl group, the butyl groups preferably substitute the phenyl group in one or more of the 2-position, 4-position, and the 6-position, although meta substitutions (3- and/or 5-positions) are also contemplated. In embodiments wherein the aryl moiety is a di-substituted phenyl group, the butyl groups may substitute the phenyl group in the 2- and 6-positions. More preferably, however, the butyl groups substitute the phenyl group in the 2- and 4-positions, as shown in structure (V) above. In embodiments wherein the aryl moiety is a tri-substituted phenyl group, the butyl groups preferably substitute the phenyl group in the 2-, 4- and 6-positions or in the 2-, 4-, and 5-positions.

Referring to the phosphites of structure (I), in one embodiment, the alkylaryl moieties, e.g., $R_1$, $R_2$, and $R_3$, are independently selected alkylated aryl groups of the structure:

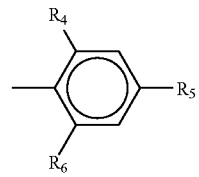

(VI)

wherein $R_4$, $R_5$, and $R_6$ are independently selected from the group consisting of hydrogen and $C_1$-$C_8$ alkyl, e.g., methyl, ethyl, propyl, butyl, amyl, hexyl, heptyl, octyl, and isomers thereof, e.g., isopropyl, tert-butyl, tert-amyl, neo-amyl, preferably butyl and its isomers, provided that at least one of $R_4$, $R_5$, and $R_6$ is an butyl group, e.g., n-butyl, t-butyl, iso-butyl or sec-butyl. In a preferred embodiment, $R_4$ and $R_6$ are hydrogen, and $R_5$ is an butyl group for at least some of the phosphite compounds in the phosphite composition as shown in structure (IV) above. Additionally, the phosphite composition preferably comprises at least some phosphite compounds in which the ortho and para positions, e.g., $R_5$ and $R_6$, are butyl groups and $R_4$ is hydrogen, as shown in structure (V) above. Preferably, the butyl groups have no α-hydrogen atoms.

As indicated by formula (I), three respective butylaryl ester groups are associated with each phosphorus atom. If a first portion of the aryl moieties are mono-butyl substituted, and a second portion of the aryl moieties are di-butyl substituted, then four phosphite compounds are possible, i.e., a tris(dibutylaryl) phosphite, a tris(monobutylaryl) phosphite, a bis(dibutylaryl)monobutylaryl phosphite, and a bis(monobutylaryl)dibutylaryl phosphite. According to preferred embodiments, as indicated above, the phosphite composition comprises at least two of these species and is a liquid at ambient conditions.

In another embodiment, $R_1$, $R_2$, and $R_3$ of structure (I) are independently selected alkylated aryl groups of the structure:

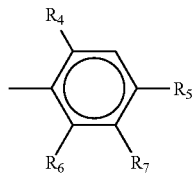

(VII)

wherein $R_4$, $R_5$, and $R_6$ are defined above and $R_7$ is hydrogen or methyl, provided that one of $R_4$, $R_5$, $R_6$, and $R_7$ is methyl and that at least two of $R_4$, $R_5$, $R_6$, and $R_7$ are not hydrogen. Such phosphites may be formed, for example, by the reaction of one or more butylated cresol compounds, e.g., one or more of butylated ortho-, meta- and/or para-cresol, with $PCl_3$, as discussed in greater detail below. Similarly, in another embodiment, two of $R_4$, $R_5$, $R_6$, and $R_7$ are methyl. Thus, the alkylated aryl group may be a xylyl group.

In various optional embodiments, the alkylated aryl groups for $R_1$, $R_2$, and $R_3$ are provided as shown in Table 1. This listing, of course, is exemplary and is not exhaustive. The phosphite compositions of the invention, in some embodiments, may comprise any two or more of these compounds, in amounts sufficient that the phosphite composition is a liquid at ambient conditions. In one embodiment, the butyl groups are sec-butyl. These groups may be present when an n-butylene is utilized to produce the intermediate alkylate composition. In another embodiment, the butyl groups are tert-butyl and/or iso-butyl. These groups may be present when an iso-butylene is utilized to produce the intermediate alkylate composition.

TABLE 1

| # | $R_1$ | | | $R_2$ | | | $R_3$ | | |
|---|---|---|---|---|---|---|---|---|---|
|   | $R_4$ | $R_5$ | $R_6$ | $R_4$ | $R_5$ | $R_6$ | $R_4$ | $R_5$ | $R_6$ |
| 1 | H | t-butyl | H | H | sec-butyl | H | H | sec-butyl | H |
| 2 | t-butyl | t-butyl | H | sec-butyl | sec-butyl | H | sec-butyl | sec-butyl | H |
| 3 | t-butyl | H | H | sec-butyl | H | H | sec-butyl | H | H |
| 4 | H | t-butyl | H | H | iso-butyl | H | H | iso-butyl | H |
| 5 | t-butyl | t-butyl | H | iso-butyl | iso-butyl | H | iso-butyl | iso-butyl | H |
| 6 | t-butyl | H | H | iso-butyl | H | H | iso-butyl | H | H |
| 7 | H | t-butyl | H | H | sec-butyl | H | H | iso-butyl | H |
| 8 | t-butyl | t-butyl | H | sec-butyl | sec-butyl | H | H | iso-butyl | H |
| 9 | t-butyl | H | H | sec-butyl | H | H | iso-butyl | iso-butyl | H |
| 10 | H | t-butyl | H | H | iso-butyl | H | H | sec-butyl | H |
| 11 | t-butyl | t-butyl | H | iso-butyl | iso-butyl | H | sec-butyl | sec-butyl | H |
| 12 | t-butyl | H | H | iso-butyl | H | H | sec-butyl | H | H |

Phosphites

In various embodiments, the inventive phosphite composition comprises at least two different butylaryl phosphite compounds, e.g., at least three different butylaryl phosphite compounds, or at least four different butylaryl phosphite compounds, of structure (I). The phosphite composition comprises at least two phosphite compounds that contain a combination of the above-mentioned butylaryl groups, e.g., monobutylaryl groups, dibutylaryl groups, tributylaryl groups or a mixture thereof. As indicated above, in addition to containing at least two different butylaryl phosphite compounds, the phosphite compositions may comprise one or more non-butyl alkylaryl phosphite compounds, so long as the overall phosphite composition is liquid at ambient conditions. In the preferred embodiment, the inventive phosphite composition comprises at least two different butylaryl phosphite compounds selected from the group consisting of a tris(dibutylaryl)phosphite, a tris(monobutylaryl) phosphite, a bis(dibutylaryl)monobutylaryl phosphite, and a bis(monobutylaryl)dibutylaryl phosphite.

An exemplary tris(dibutylaryl)phosphite corresponds to the following formula:

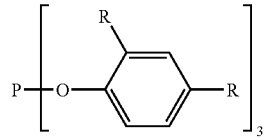

(VIII)

wherein each R is a butyl group, the same or different, preferably selected from e.g., n-butyl, tert-butyl, iso-butyl or sec-butyl. The butyl groups, R, may differ from one another on a given dibutylaryl moiety and/or between adjacent dibutylaryl moieties, or a combination thereof.

Although the exemplary tris(dibutylaryl)phosphite compound (VIII) is uniformly o/p substituted, other substitutions are also possible. For example, in another embodiment, two dibutylaryl ester groups on a given phosphite molecule may be o/p substituted, and the third dibutylaryl ester group may be o/m substituted. Of course, other combinations are possible. Additionally or alternatively, some tris(dibutylaryl) phosphite compounds in the phosphite composition may be uniformly substituted with o/p dibutylaryl ester groups, while other tris(dibutylaryl)phosphite compounds in the phosphite composition may be uniformly substituted with dibutylaryl ester groups that are substituted in different positions, e.g., o/m or m/m. It is preferred, however, that the majority, e.g., at least 80%, at least 90%, or at least 95% of the dibutylaryl ester groups in the overall phosphite composition are o/p-substituted, based on the total number of dibutylaryl ester groups in the phosphite composition (i.e., excluding any monobutylated phosphite groups).

The preferred tris(dibutylaryl) phosphite species is tris(2,4-di-tert-butylphenyl) phosphite. Thus, the phosphite composition optionally comprises tris(2,4-di-tert-butylphenyl) phosphite in an amount greater than 80 wt. %, greater than 90 wt. % or greater than 95 wt. %, based on the total number of tris(dibutylaryl)phosphite species in the phosphite composition. Of course, other tris(dibutylaryl)phosphites are also possible.

An exemplary tris(monobutylaryl) phosphite, e.g., tris(4-mono-tert-butylphenyl) phosphite corresponds to the following formula:

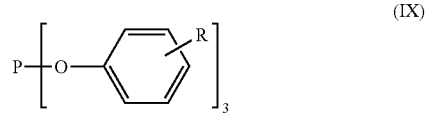

(IX)

wherein R may be in the ortho, meta or para position, or a combination thereof, and wherein each R is a butyl group, the same or different from the R on adjacent monobutylaryl ester groups, preferably selected from n-butyl, tert-butyl, iso-butyl or sec-butyl.

For the tris(monobutylaryl) phosphites, some monobutylaryl ester groups may be substituted in a manner different from other monobutylaryl ester groups on the same phosphite molecule. For example, one monobutylaryl moiety may be ortho substituted, and an adjacent monobutylaryl moiety on the same molecule may be para substituted. In addition, some tris(monobutylaryl)phosphite molecules may be uniformly monosubstituted in a manner different from other tris (monobutylaryl)phosphite molecules. For example, some tris (monobutylaryl)phosphite molecules may be uniformly para substituted, while other tris(monobutylaryl)phosphite molecules may be uniformly ortho substituted or uniformly meta substituted. It is preferred, however, that the majority, e.g., at least 50%, at least 90%, or at least 95%, of the monobutylaryl ester groups are para-substituted, based on the total number of monobutylaryl ester groups (i.e., excluding any polybutylaryl ester groups).

The preferred tris(monobutylaryl) phosphite is tris(4-tert-butylphenyl) phosphite. Thus, the phosphite composition optionally comprises tris(4-tert-butylphenyl) phosphite in an amount greater than 80 wt. %, greater than 90 wt. % or greater than 95 wt. %, based on the total number of tris(monobutylaryl)phosphite species in the phosphite composition. Of course, other tris(monobutylaryl)phosphites are also possible.

An exemplary bis(dibutylaryl)monobutylaryl phosphite, e.g., bis(2,4-di-tert-butylphenyl)4-tert-butylphenyl phosphite corresponds to the following formula:

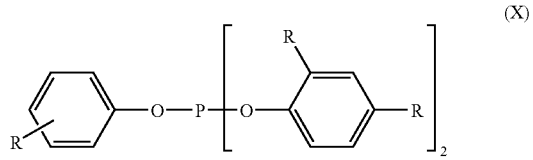

(X)

wherein R on the monobutylaryl moiety may be in the ortho, meta or para position, or a combination thereof for different bis(dibutylaryl)monobutylaryl phosphite compounds in the phosphite composition, and wherein each R is a butyl group, the same or different, preferably selected from n-butyl, tert-butyl, iso-butyl and sec-butyl. Although the dibutylaryl phosphite moieties in the exemplary bis(dibutylaryl)monobutylaryl phosphite compound (X) above are uniformly o/p substituted, other substitutions are also possible as discussed above in connection with the tris(dibutylaryl)phosphite compound (VIII).

The preferred bis(dibutylaryl)monobutylaryl phosphite is bis(2,4-di-tert-butylphenyl)4-tert-butylphenyl phosphite, and the phosphite composition preferably comprises bis(2,4-di-tert-butylphenyl)4-tert-butylphenyl phosphite in an amount greater than 80 wt. %, greater than 90 wt. % or greater than 95 wt. %, based on the total number of bis(dibutylaryl)monobutylaryl phosphite species in the phosphite composition. Of course, other bis(dibutylaryl)monobutylaryl phosphites are also possible.

An exemplary bis(monobutylaryl)dibutylaryl phosphite, e.g., bis(4-tert-butylphenyl)2,4-di-tert-butylphenyl phosphite corresponds to the following formula:

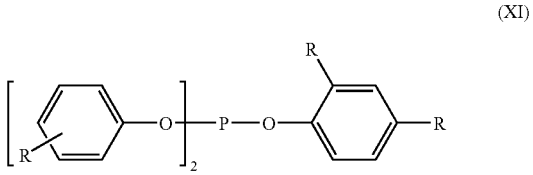

(XI)

wherein R on the monobutylaryl moieties may be in the ortho, meta or para position, or a combination thereof for different bis(monoalkylaryl)dialkylaryl phosphite compounds in the phosphite composition and/or for adjacent monobutylaryl moieties on the same phosphite compound, and wherein each R is a butyl group, the same or different, preferably selected from n-butyl, tert-butyl, iso-butyl and sec-butyl. Although the dibutylaryl phosphite moiety in the exemplary bis(monoalkylaryl)dialkylaryl phosphite compound (XI) above is o/p substituted, other substitutions are also possible as discussed above.

The preferred bis(monobutylaryl)dibutylaryl phosphite is bis(4-tert-butylphenyl)2,4-di-tert-butylphenyl phosphite, and the phosphite composition preferably comprises bis(4-tert-butylphenyl)2,4-di-tert-butylphenyl phosphite in an amount greater than 80 wt. %, greater than 90 wt. % or greater than 95 wt. %, based on the total number of bis(monobutylaryl)dibutylaryl phosphite species in the phosphite composition. Of course, other bis(monobutylaryl)dibutylaryl phosphites are also possible.

In some preferred embodiments of the present invention, the phosphite composition comprises at least two phosphites selected from the group consisting of tris(4-tert-butylphenyl) phosphite, tris(2,4-di-tert-butylphenyl) phosphite, bis(4-tert-butylphenyl)2,4-di-tert-butylphenyl phosphite, and bis(2,4-di-tert-butylphenyl)4-tert-butylphenyl phosphite, wherein the composition is a liquid at ambient conditions. Preferably, the phosphite composition comprises at least two of these compounds, at least three of these compounds or all four of these compounds, in an amount greater than 80 wt. %, 90 wt. % or 95 wt. %, based on the total weight of all phosphites in the phosphite composition. Of course, a minor amount of other species, phosphite or non-phosphite, may be present, e.g., one or more of bis(4-tert-butylphenyl)2-tert-butylphenyl phosphite or bis(2,4-di-tert-butylphenyl)2-tert-butylphenyl phosphite and the like.

In some embodiments, the phosphite compositions have an overall phosphorus content that is equal to or greater than that of TNPP, e.g., at least 4.0 mol %, e.g., at least 4.5 mol % at least 4.8 mol %, or at least 5.1 mol %. In terms of ranges, the overall phosphorus content of the phosphite composition may range from 4.0 to 6.5 mol %, e.g., from 4.5 to 6.0 mol %, or from 5.1 to 5.8 mol % of all phosphorous containing compounds in the phosphite composition. It is contemplated that the overall phosphorus content may be reduced by decreasing the content of the tris(dibutylaryl) phosphite. Conversely, the overall phosphorus content may be increased by increasing the content of the tris(monobutylaryl) phosphite. It is also contemplated that, by utilizing butylaryl substituted phosphites, the overall phosphite content of the phosphite composition can be increases, as compared to phosphite compositions utilizing phosphites substituted with aryl groups substituted with higher carbon moieties, e.g., amyl groups, hexyl groups, heptyl groups, octyl groups, etc.

The relative amounts of the respective phosphite components contained in the phosphite compositions of the invention may vary somewhat so long as the phosphite composition is a liquid at ambient conditions. In terms of ranges, for example, the phosphite composition preferably comprises tris(monobutylaryl)phosphites, e.g., tris(4-tert-butylphenyl) phosphite, in an amount from 35-75 wt %, e.g., from 45-65 wt %, or from 54-63 wt %, and bis(monobutylaryl)dibutylaryl phosphites, e.g., bis(4-tert-butylphenyl)-2,4-di-tert-butylphenyl)phoshite, in an amount from 21-47 wt %, e.g., from 26-42 wt %, or from 31-37 wt %. Optionally, the phosphite composition further comprises tris(dibutylaryl)phosphites and/or bis(dibutylaryl)monobutylaryl phosphites. If present, the tris(dibutylaryl)phosphites, e.g., tris(2,4-di-tert-butylphenyl)phosphite, preferably are present in an amount of from 0-3 wt %, e.g., from 0-2 wt %, or from 0-1 wt %. If present, the bis(dibutylaryl)monobutylaryl phosphites, e.g., bis(2,4-di-tert-butylphenyl)-4-tert-butylphenyl phosphite, are preferably present in an amount of from 5-15 wt %, e.g., from 3-10 wt %, or from 5-8 wt %. Unless otherwise indicated, wt % is based on the total weight of all phosphites the composition. As shown above, in one embodiment, the ranges for the components of the inventive butylaryl phosphite compositions are specific. In contrast, the component ranges for other alkylaryl phosphites, e.g., propyl aryl phosphites, amylaryl phosphites, hexylaryl phosphites, or octylaryl phosphites, may be broader and not as well defined. Thus, it is surprising and unexpected that the ranges for the components of the inventive butylaryl phosphites are specific and well defined.

In terms of weight ratios, the phosphite composition optionally has a weight ratio of tris(monobutylaryl)phosphites to the combination of bis(monobutylaryl)dibutylaryl phosphites, (dibutylaryl)monobutylaryl phosphites and tris(dibutylaryl)phosphites of from 1:2 to 3:1, e.g., from 5:6 to 9:5, or from 6:5 to 9:5.

The phosphite composition optionally has a weight ratio of bis(monobutylaryl)dibutylaryl phosphites to the combination of tris(monobutylaryl)phosphites, bis(dibutylaryl)monobutylaryl phosphites and tris(dibutylaryl)phosphites of from 1:4 to 1:1, e.g., from 1:3 to 3:4, or from 4.5:10 to 6:10.

The phosphite composition optionally has a weight ratio of bis(dibutylaryl)monobutylaryl phosphites to the combination of tris(monobutylaryl)phosphites, bis(monobutylaryl)dibutylaryl phosphites, and tris(dibutylaryl)phosphites of from 1:33 to 1:15, from 1:33 to 1:10, or from 1:20 to 1:5, optionally less than 1:33, less than 1:15, or less than 1:10.

The phosphite composition optionally has a weight ratio of tris(dibutylaryl)phosphites to the combination of bis(monobutylaryl)dibutylaryl phosphites, bis(dibutylaryl)monobutylaryl phosphites, and tris(monobutylaryl)phosphites of from 1:1,000 to 2:5, e.g., from 1:500 to 1:20, or from 1:500 to 1:100, or optionally less than 1:1,000, e.g., less than 1:500, or less than 1:100.

The viscosity of the phosphite composition may vary depending on the relative amounts of the various phosphite compounds contained therein. In some exemplary embodiments, the phosphite composition has a viscosity less than 50,000 cSt, e.g., less than 35,000 cSt, less than 25,000 cSt, less than 15,000 cSt, or less than 10,000 cSt, these viscosities being measured at 30° C. In terms of ranges, viscosity of the composition may range from 1 cSt to 50,000 cSt, from 1,000 cSt to 35,000 cSt, from 2,000 cSt to 25,000 cSt, from 3,000 cSt to 20,000 cSt, or from 7,000 cSt to 12,000 cSt, these viscosities being measured at 30° C. In one embodiment, the composition has a viscosity less than 20,000 cSt, e.g., less than 15,000 cSt, less than 10,000 cSt, less than 5,000 cSt, or less than 3,000 cSt, these viscosities being measured at 40° C. In terms of ranges, viscosity of the composition may range from 1 cSt to 20,000 cSt, from 1,000 cSt to 10,000 cSt, from 1,000 cSt to 5,000 cSt, or from 1,000 cSt to 3,500 cSt, these viscosities being measured at 40° C. In one embodiment, the composition has a viscosity less than 1,000 cSt, e.g., less than 500 cSt, less than 300 cSt, less than 270 cSt, or less than 250 cSt, all viscosities being measured at 60° C. In terms of ranges, viscosity of the composition may range from 1 cSt to 1,000 cSt, from 100 cSt to 500 cSt, from 100 cSt to 400 cSt, or from 200 cSt to 300 cSt, all viscosities being measured at 60° C.

In some embodiments, the inventive phosphite compositions have relatively high viscosities, e.g., greater than 1,000 cSt, greater than 3,000 cSt, greater than 5,000 cSt, greater than 7,000 cSt, greater than 9,500 cSt, greater than 12,000 cSt, greater than 20,000 cSt, or greater than 40,000 cSt, these viscosities being measured at 30° C. In one embodiment, the phosphite composition has a viscosity greater than 500 cSt, e.g., greater than 1,000 cSt, greater than 1,200 cSt, greater than 1,500 cSt, greater than 2,000 cSt, greater than 3,000 cSt, greater than 4,000 cSt, or greater than 10,000 cSt, these viscosities being measured at 40° C. In one embodiment, the phosphite composition has a viscosity greater than 500 cSt, greater than 700 cSt, greater than 900 cSt, or greater than 1,000 cSt, these viscosities being measured at 50° C. In one embodiment, the phosphite compositions has a viscosity greater than 150 cSt, e.g., greater than 175 cSt, greater than 200 cSt, greater than 225 cSt, or greater than 270 cSt, these viscosities being measured at 60° C. Of course, while such phosphite compositions may have high viscosities, the compositions are still in the liquid state and remain stable after three freeze/thaw cycles, e.g., the compositions are not metastable. In some aspects, the high viscosity phosphites of the invention have viscosities that are higher, e.g., more than 10% higher, more than 20% higher, more than 30% higher, more than 50% higher or more than 100% higher, than phosphite compositions comprising aryl moieties substituted with groups other than butyl groups, e.g., propyl, amyl, hexyl, heptyl, or octyl.

In addition, the viscosity of the inventive phosphite compositions may be characterized by the temperature required for the compositions reach a viscosity of 300 cSt (or less). As an example, the inventive phosphite composition may be heated to 50° C. or greater, e.g., 60° C. or greater, 70° C. or greater, or 80° C. or greater, before achieving a viscosity of 300 cSt.

As suggested above, the phosphite compositions of the invention may be characterized based on how the aryl moieties, e.g., phenyl moieties, are substituted, e.g., butyl (e.g., t-butyl) substituted, as a whole. For example, in one embodiment, a majority of the aryl moieties are mono substituted in the para-position, e.g., at least 60%, at least 70%, at least 80%, or at least 85% mono substituted in the para-position, optionally from 60 to 90%, e.g., from 65 to 85 or from 70 to 85% mono substituted in the para-position, based on the number of aryl moieties in the phosphite composition. In other embodiments, some of the aryl moieties are disubstituted, e.g., ortho- and para-disubstituted, at least in part. Preferably at least 5% of the aryl moieties are ortho- and para-disubstituted, e.g., at least 10% ortho- and para-disubstituted, at least 12% ortho- and para-disubstituted, at least 15% ortho- and para-disubstituted, or at least 20% ortho- and para-disubstituted, optionally from 5 to 30% ortho- and para-disubstituted, e.g., from 10 to 25 or from 12 to 25% ortho- and para-disubstituted, based on the total number of aryl moieties in the phosphite composition. In other embodiments, the ratio of monoamylaryl groups to diamylaryl groups ranges from 7:1 to 1:1, e.g., from 5.5:1 to 1:1, or from 5:1 to 2:1.

Depending largely on how the phosphites are manufactured, the phosphite compounds may be similarly substituted with butyl groups on each aryl moiety per molecule. That is, some phosphite compounds may be exclusively monosubstituted, e.g., para-substituted, and/or some phosphite compounds may be exclusively disubstituted, e.g., ortho and para disubstituted, provided that at least some portion of the aryl moieties in the overall phosphite composition are mono-substituted and at least some portion of the aryl moieties in the overall phosphite composition are disubstituted. For example, some or all of the phosphite molecules may contain both mono and disubstituted aryl moieties. Additionally or alternatively, the phosphite composition may comprise phosphite molecules that are exclusively monosubstituted, e.g., para substituted, and/or phosphite molecules that are exclusively disubstituted, e.g., ortho- and para-disubstituted.

As indicated above, the phosphite compositions of the invention includes phosphite compounds having aryl moieties that are monobutylated and dibutylated. Ideally, few if any of the aryl moieties are tri-substituted. For example, in some embodiments, fewer than 3 wt %, e.g., fewer than 2 wt %, fewer than 1 wt %, fewer than 0.5 wt %, or fewer than 0.1 wt %, of the aryl moieties are trisubstituted. Although preferably substantially free of trisubstituted aryl moieties, optionally from 0 wt % to 10 wt %, from 0 wt % to 3 wt % or from 0.5 wt % to 1.5 wt % of the aryl moieties may be trisubstituted, based on the total aryl moieties in the phosphite composition. In another embodiment, the phosphite compositions are completely free of trisubstituted aryl moieties.

Similarly, it is preferred that few if any of the aryl moieties are monosubstituted in the ortho-position. Preferably, the aryl moieties that are monosubstituted in the ortho position are present, if at all, in an amount less than 3 wt %, e.g., less than 2 wt %, or less than 1 wt %.

Preferably, the phosphite composition has a low level or is substantially free of phenolics (e.g., phenols, cresols or xylenols), whether alkylated or unalkylated, which is referred to herein as "free phenolics" when contained in the phosphite composition. In terms of amounts, the phosphite composition preferably comprises less than 5 wt. %, e.g., less than 3 wt. % or less than 1 wt. %, of free phenolics, based on the total weight of the phosphite composition. Any free phenolics, for example, may be removed by distillation. Extremely low levels of free phenolics may be achieved, for example, by employing a wiped-film molecular (Short-Path) still, wiped film evaporator (WFE), thin film evaporator, or similar equipment. In terms of amounts, the phosphite composition may comprise less than 0.5 wt. %, e.g., less than 0.2 wt. % or less than 0.1 wt. %, of free phenolics, based on the total weight of the phosphite composition.

In other embodiments, a minor amount of free phenolics may be beneficial, for example, as a viscosity reducing agent. Thus, in one embodiment, the phosphite composition comprises a minor amount of free phenolics, e.g., from 1 to 4 weight percent, e.g., from 2 to 3 weight percent, based on the total weight of the phosphite composition.

In addition, the phosphite composition is preferably substantially free of phosphite compounds having unsubstituted aryl moieties, e.g., triphenylphosphites, bis(phenyl)alkylphenyl phosphites or bis(alkylphenyl)phenyl phosphites. In terms of amounts, the phosphite composition preferably comprises less than 2 wt. %, e.g., less than 1 wt. % or less than 0.5 wt. %, phosphite compounds having at least one unsubstituted aryl moiety, based on the total weight of the phosphite composition.

In other embodiments, the phosphite composition is substantially free of phosphite compounds having aryl groups that are substituted with alkyl groups having hydrogens in the α position. That is, in preferred embodiments, at least 95%, at least 98% or at least 99% of the aryl moieties are substituted with alkyl groups having tertiary α-carbons, most preferably tert-butyl.

In some preferred embodiments, the phosphite composition includes one or more hydrolytic stabilizers. Preferred stabilizers include amines of the structure:

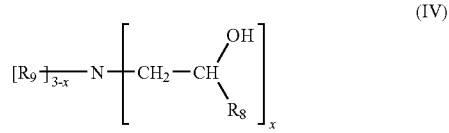

(IV)

wherein x is 1, 2 or 3; $R_8$ is selected from the group consisting of hydrogen, and straight or branched $C_1$-$C_6$ alkyl, and $R_9$ is selected from the group consisting of straight or branched $C_1$-$C_{30}$ alkyl. Preferably $R_8$ is selected from the group consisting of straight or branched $C_1$-$C_4$ alkyl, e.g., methyl or ethyl. Preferably $R_9$ is selected from the group consisting of straight or branched $C_5$-$C_{20}$ alkyl, e.g., straight or branched $C_{10}$-$C_{20}$ alkyl or straight or branched $C_{12}$-$C_{18}$ alkyl. In one embodiment, x is 1 and $R_9$ is straight or branched $C_5$-$C_{20}$ alkyl, e.g., $C_{12}$-$C_{18}$ alkyl. In one embodiment, x is 2 and $R_9$ is straight or branched $C_{10}$-$C_{20}$ alkyl, e.g., $C_{12}$-$C_{18}$ alkyl.

In one aspect the amine is selected from the group consisting of triethanolamine, triisopropanolamine, diethanolamine, diisopropanolamine, and tetraisopropanolethylenediamine.

In another aspect the amine is selected from the group consisting of octyl-bis(2-ethanol)amine, nonyl-bis(2-ethanol)amine, decyl-bis(2-ethanol)amine, undecyl-bis(2-ethanol)amine, dodecyl-bis(2-ethanol)amine, tridecyl-bis(2-ethanol)amine, tetradecyl-bis(2-ethanol)amine, pentadecyl-bis(2-ethanol)amine, hexadecyl-bis(2-ethanol)amine, heptadecyl-bis(2-ethanol)amine, octadecyl-bis(2-ethanol)amine, octyl-bis(2-propanol)amine, nonyl-bis(2-propanol)amine, decyl-bis(2-propanol)amine, undecyl-bis(2-propanol)amine, dodecyl-bis(2-propanol)amine, tridecyl-bis(2-propanol)amine, tetradecyl-bis(2-propanol)amine, pentadecyl-bis(2-propanol)amine, hexadecyl-bis(2-propanol)amine, heptadecyl-bis(2-propanol)amine, octadecyl-bis(2-propanol)amine, and isomers thereof. Commercially available amines include Armostat™ 300 and Armostat 1800 manufactured by Akzo Nobel Polymers.

Additional hydrolytic stabilizers include epoxies such as epoxidized soybean oil (ESBO) commercially available as Drapex™ 39, Drapex 392, Drapex 4.4, and Drapex 6.8 (Chemtura Corp.).

The amine may be present in an amount of from 0.01 to 5 wt. %, e.g., from 0.1 to 1.5 wt. % or from 0.2 to 0.8 wt. %, based on the total weight of the phosphite composition.

Liquid Characteristics

As indicated above, the phosphite composition is a liquid at ambient conditions. As used herein, by "liquid," it is meant that the phosphite composition remains liquid after at least three "freeze/thaw" cycles as opposed to "meta-stable liquids," which do not remain liquid after three or fewer cycles. A freeze/thaw cycle is defined as follows: 1) An ambient temperature composition is stirred for 0.5 hours; 2) The stirred composition is then refrigerated at about 5° C. for three days; and 3) The refrigerated composition is then brought to ambient temperature and held at ambient for 3 days. Upon completion of step 3, the composition is checked for solids content, e.g., crystallization. Completion of steps 1-3 defines one freeze/thaw cycle.

As noted above, it is a feature of the present invention that the phosphite composition is in liquid physical form at room temperature. This is clearly surprising, given that the prior art teaches several examples of solid phosphites, the components of which are separately solids at ambient condition, (See JP 59030842; WO 9303092; CA 2,464,551). In the present invention, in contrast, the phosphite compositions are liquid even though the individual components are solid. Table 2 provides the melting points of several different phosphites within the scope of the present invention.

TABLE 2

| Phosphite | Melting Point |
|---|---|
| Tris 4-tert-butylphenyl phosphite | 75-76° C. |
| Tris 2,4-di-tertbutylphenyl phosphite | 181-184° C. |
| Bis(4-tert-butylphenyl)-2,4-di-tert-butylphenyl phosphite | 63-65° C. |
| Bis(2,4-di-tert-butylphenyl)-4-tert-butylphenyl phosphite | 100-103° C. |

Processes for Making Phosphite compositions

The present invention also relates to methods for making the above-described liquid phosphite compositions. In one embodiment, the liquid phosphite compositions may be made in the direct reaction of a phosphorus trihalide, e.g., phosphorus trichloride, and two or more alkylated phenolics. The terms "phenolics" and "phenolic compounds" refers to aromatic compounds having at least one hydroxyl group, and includes, for example, phenols, cresols, xylenols, and mixtures thereof.

The alkylate composition may be formed by contacting one or more phenolics with one or more olefins in the presence of a catalyst and under conditions effective to form the alkylate composition. The one or more olefins preferably contain from 1 to 18 carbons, e.g., from 1 to 8 carbons, or from 4 to 6 carbons. As an alternative to using an olefin alkylating agent, one or more alkyl halides, alcohols, MTBE or TAME may be employed. The alkylating agent that is employed may comprise or be derived from a hydrocarbon stream comprising alkanes and alkenes, such as a petrochemical raffinate stream from a $C_4$ or $C_5$ fraction, or a dehydrogenation reaction product of an alkane, e.g., isobutane or isopentane. In this aspect, the alkanes pass through the alkylating process unaltered and may be easily separated from the product alkylate composition.

The ratio of olefin to phenolics preferably is such that the resulting alkylate composition is suitable for conversion to the desired phosphite composition when reacted with a phosphorous halide. In some exemplary embodiments, the olefin to phenolic compound mole ratio ranges from 1:1 to 6:1, e.g., from 1.1:1 to 2:1 or from 1.25:1 to 1.4:1, although these ratios may very somewhat depending, for example, on the catalyst employed in the alkylation process and the desired composition and viscosity for the ultimately formed phosphite composition.

In addition, the composition of phenols, e.g., butylphenols, can be selected and/or adjusted so as to produce a desired liquid phosphite composition having a target viscosity and/or a target stability level. Of course, other factors, e.g., phenolic excess, reaction temperature profile, final residual phenolic content, choice of catalyst, etc., can also affect the resultant phosphite compositions.

In a preferred embodiment, the alkylate composition comprises 4-butyl phenol, 2,4-di-butyl phenol and, optionally, 2-butyl phenol and/or non-alkylated phenol. In terms of ranges, the monobutyl phenol, e.g., 4-tert-butyl phenol, optionally is present in an amount ranging from 50 wt % to 99 wt %, e.g., from 55 wt % to 90 wt %, from 60 wt % to 85 wt %, from 60 wt % to 80 wt %, or from 65 wt % to 80 wt %. In terms of ranges, the dibutyl phenols, e.g., 2,4-di-tert-butyl phenol, optionally is present in an amount ranging from 1 wt % to 50 wt %, e.g., from 10 wt % to 41 wt %, from 15 wt % to 35 wt %, or from 15 wt % to 26 wt %. The weight percentages are based on the total weight of the alkylate composition. In addition, the ratio of 4-tert-butylphenol to 2,4-di-tert-butylphenol can be selected or adjusted so as to produce the desired liquid phosphite composition. Preferably, the ratio of 4-tert-butylphenol to 2,4-di-tert-butylphenol ranges from 2:1 to 10:1, e.g., from 3:1 to 7:1, or from 4:1 to 6:1. Thus, by adjusting the components of the alkylate composition and/or the ratio of these components, stable liquid compositions of phosphites can be achieved. Of course, other factors, e.g., phenolic excess, reaction temperature profile, final residual phenolic content, etc., can also affect the resultant phosphite compositions.

Although conditions for the alkylation process may vary widely, in some preferred embodiments, the reaction of the phenol and the olefin may occur in an inert atmosphere (e.g., under nitrogen) at a temperature of from 60 to 160° C., e.g., from 70 to 145° C. or from 80 to 140° C. The reaction is preferably performed at a pressure of from 0.2 to 10 atm, e.g., from 0.2 to 5 atm or from 0.2 to 4 atm. In a batch reaction, the reaction time may last from 1 to 12 hours, e.g., from 2 to 10 hours, or from 3 to 5 hours. In a continuous reaction, the residence time may be from 0.1 to 5 hours, e.g., from 0.2 to 4 hours or from 0.5 to 1 hour. The alkylation preferably is performed in the presence of a catalyst. The catalyst may, for example, be selected from the group consisting of acid clay catalyst, cationic ion exchange resins, Brönsted acids, e.g., sulfuric acid, Trifluoromethanesulfonic acid (triflic acid) and phosphotungstic acid, or Lewis acids, e.g., $BF_3$ Suitable commercial acid clay catalysts include Fulcat™ 22B (Rockwood Additives). In one embodiment, the sulfonic acid-type cation-exchange resin catalyst useful in the present invention can be, for example, a sulfonated styrene-divinyl benzene copolymer, a sulfonated crosslinked styrene polymer, a phenol formaldehyde-sulfonic acid resin, or a benzene formaldehyde-sulfonic acid resin. Cation exchange resins useful in the present invention include for example styrene-divinylbenzene types of strong acid ion exchange resins such as Dowex™ 50WX4, Dowex 50WX2, Dowex M-31, Dowex Monosphere M-31, Dowex DR-2030 and Dowex Monosphere DR-2030 catalysts (Dow Chemical). Other appropriate resins include: Amberlyst™ 15, Amberlyst 131, Amberlyst 35, Amberlyst 36, and A21 (Rohm and Hass, subsidiary of Dow); Diaion™ WA30, Diaion SK104, Diaion SK1B, Diaion PK208, Diaion PK212 and Diaion PK216 (Mitsubishi); Tulsion™ T-38, Tulsion T-62, Tulsion T-66, Tulsion T-3825 and Tulsion T-3830 (Thermax); Lewatit™ K1131, Lewatit K1221, Lewatit K1261 and Lewatit SC 104 (Sybron Chemicals); Indion™ 180 and Indion 225 (Ion Exchange (India) Limited); and Purolite™ CT-175, Purolite™ CT-169, and Purolite™ CT-275 (Purolite). Dowex DR2030™ and Fulcat 22B™ are preferred.

It is contemplated that alkyl substitution of the aryl groups may be varied by selection of the catalyst used to alkylate the aryl group. For example, in embodiments where an ortho substitution is desired, a milder catalyst, e.g., aluminum phenate or $BF_3$, is utilized. Alternatively, where a meta substitution is desired, a stronger catalyst, e.g., triflic acid, is utilized.

It is contemplated that the alkylation process will produce an alkylate composition having an amount of impurities, e.g., tri-butyl phenol or 2,4,6-tri-tert-butylphenol. 2,4,6-tri-tert-butylphenol is restricted in some parts of the world, e.g., Japan. As such, the use thereof is typically minimized, preferably avoided altogether. The amount of 2,4,6-tri-tert-butylphenol may range from 0.1 wt % to 10 wt %, e.g., from 0.1 wt % to 5 wt %, from 0.5 wt % to 3 wt %, or from 0.5 wt % to 2 wt %. In terms of limits, the tri-butyl phenol may be present in amounts less than 3 wt %, e.g., less than 1 wt %, less than 0.5 wt %, or less than 0.1 wt %. It is contemplated that safety standards in foreign countries, e.g., Japan, may require reduced amounts (if any) tri-butyl phenols in the resultant phosphite. Thus, in one embodiment, where lower amounts of trialkylated phenol, e.g., 2,4,6-tri-tert-butylphenol, are required, the tri-butylphenol may be present in amounts less than 10 wppm, e.g., less than 5 wppm, less than 2 wppm, less than 1 wppm, or less than 0.5 wppm. In such situations, the tri-butyl phenol may be separated from the alkylate composition. Conventional processes, such as, e.g., distillation, may be used to achieve the separation. In certain aspects, distillation reduces the 2,4,6-tri-tert-butyl phenol content to below 5 wt %, e.g., below 3 wt %, below 2 wt %, below 1 wt %, below 0.5 wt %, below 0.1 wt %, or below 0.05 wt %.

It is further contemplated that the alkylation process will produce an alkylate composition having an amount of colored impurities, although a clear alkylate is preferred. Colored impurities are undesirable because color generated in the alkylate can be carried through into the final phosphite composition. Accordingly, in such situations, the colored impurities may be separated from the alkylate composition.

In one embodiment, a batch alkylate synthesis takes place in a pot-type reactor. In another embodiment, the alkylate synthesis is conducted on a continuous basis in a continuous type reactor. In the continuous process, the alkylation reaction is optionally quenched using a polar solvent, water, that forms a liquid phase containing most, if not all, of the catalyst and a organic phase containing the alkylated aryl compound, which may be removed by distillation. In alternative embodiments, the reaction is conducted in a fixed bed reactor. When the continuous process takes place over a fixed bed of solid catalyst, a quenching step may not be necessary.

In one aspect of the process, any free phenolic compounds that are not reacted with the olefin may be removed from the mixture of reaction products through distillation at a temperature, for example, of from 70° C. to 160° C. and at a pressure of from 1 to 10 mbar.

In some embodiments, a mixed olefin and/or mixed phenolic feedstock may be used to form a more diverse alkylate composition, which may be desired to ultimately form a more diverse phosphite composition. Thus, a mixture of lower alkenes (e.g., two or more $C_3$-$C_6$ olefins, such as a mixture of butylene and amylenes) may be reacted with the phenolic compound either in parallel (feed in olefin A and B at the same time) or consecutively (i.e. olefin A is reacted first followed by olefin B).

As indicated above, depending on the desired composition and target viscosity for the alkylate composition as well as the ultimately formed phosphite composition, the composition of the alkylate composition may vary widely. The alkylate composition may comprise, for example, from 50 wt % to 99 wt %, e.g., from 55 wt % to 90 wt %, from 60 wt % to 85 wt %, from 60 wt % to 80 wt %, or from 65 wt % to 80 wt % of a para-alkylated phenolic compound, and from 1 wt % to 50 wt %, e.g., from 10 wt % to 40 wt %, from 15 wt % to 30 wt %, or from 15 wt % to 16 wt % of an ortho-/para-alkylated phenolic compound, wherein either or both of the para-alkylated phenolic or the ortho-/para-alkylated phenolic compounds are butylated.

In one embodiment, the alkylate composition, optionally formed from the above-described alkylate composition synthesis process, is further reacted with a phosphorus trihalide, with or without catalyst, to form a liquid phosphite composition. The phosphorus trihalide preferably is selected from phosphorus trichloride and phosphorus tribromide. When a catalyst is used, the catalyst may be selected from the group consisting of pyridine, N,N-dimethyldodecylamine, dilauryl methyl amine, trialkylamine, and the hydrochloride salts thereof. The molar ratio of alkylate composition (i.e., alkylated phenol compounds) to phosphorus trihalide preferably is from 3:1 to 5:1, e.g., from 3:1 to 4:1 or from 3.1 to 3.7:1. It is contemplated that, in cases where the phosphorus trihalide is not reacted with an excess of alkylate, e.g., an alkylate composition to phosphorus trihalide ratio less than 3:1, that there may be no free phenol remaining in the composition. In these cases, in one embodiment, phenol compounds can be added to the phosphite composition to vary the viscosity of the overall composition, as discussed above.

In one embodiment, when the alkylate composition contains at least 10 wt % free phenol, e.g., at least 15 wt % free phenol or at least 20 wt % free phenol, the viscosity of the resultant phosphite composition may be reduced by an order of magnitude.

The reaction of the alkylated phenols with a phosphorus trihalide may be conducted under an inert atmosphere (e.g., nitrogen) at a temperature of from 5 to 70° C., e.g., from 40 to 70° C. or from 50 to 70° C. The phosphorus trihalide may be charged to the reactor and the alkylate composition may be added thereto. In this case, preferably, the temperature is held at or below 70° C. during the addition of the phosphorus trihalide to the alkylate composition to prevent refluxing the phosphorus trihalide. After the addition of phosphorus trihalide, the temperature is optionally held for 10 minutes to 12 hours, e.g., from 30 minutes to 10 hours, or from 1 hour to 3 hours. The reaction preferably is conducted at a pressure of 0.8 to 4 atm, e.g., from 0.9 to 3 atm or from 1 to 2 atm. Optionally, the alkylate composition may be charged to the reactor and the phosphorus trihalide added thereto. Next, the temperature may be ramped a ramped temperature ranging from 70° C. to 250° C., e.g., from 80° C. to 225° C. or from 90° C. to 200° C. Preferably, the reaction is held at the ramped temperature for from 10 minutes to 12 hours, e.g., from 30 minutes to 10 hours, or from 1 hour to 3 hours. The reaction preferably is conducted at a reduced pressure of 0.01 to 0.5 atm, e.g. from 0.03 to 0.4 atm or from 0.04 to 0.1 atm. During the reaction time, hydrochloric or hydrobromic gas will be evolved, and may be removed by reducing the pressure to about 0.05 atm or sweeping an inert gas such as nitrogen over the reaction mixture. In one aspect the removal of such gases may be performed until the total chloride content in the reaction mixture is less than 50 wppm, e.g., less than 25 wppm or less than 10 wppm.

In one embodiment, the phosphite synthesis takes place in a pot-type reactor. In alternative embodiments, the reaction takes place in a fixed bed reactor.

In another embodiment, the phosphite synthesis is conducted on a continuous basis. Alternatively, the phosphite synthesis is conducted on a batch basis.

Although the present invention relates to a composition, the composition (and processes for producing the composition) are not meant to require a combining or mixing step. Thus, the invention contemplates any composition that simply comprises the claimed components.

In one aspect of the process, any free phenolic compounds that are not reacted with the phosphorus trihalide may be liberated from the crude phosphite composition by stripping, e.g., raising the reaction temperature, e.g., up to 275° C., e.g., up to 250° C. or up to 225° C., and in a vacuum at a pressure of 0.0001 to 0.1 atm in order to form the final phosphite composition. In one embodiment, a wiped-film molecular (Short-Path) still, wiped film evaporator (WFE), thin film evaporator, or similar equipment may be used to further remove the free cresol or phenol to the very low levels indicated above.

In one embodiment, the step of forming the phosphite composition may occur in one or more neutral solvents. Typical solvents that may be employed include toluene, xylene, methylene chloride, heptane, chloroform, and benzene.

In one embodiment, the liquid phosphite compositions of the present invention are obtained in a direct chemical reaction, in which the weight ratio of the alkylated phenolics, e.g., butylated phenolics, is adjusted to yield a phosphite composition that is a liquid at ambient conditions. A schematic of one reaction method that may be employed to form such phosphite compositions is as follows.

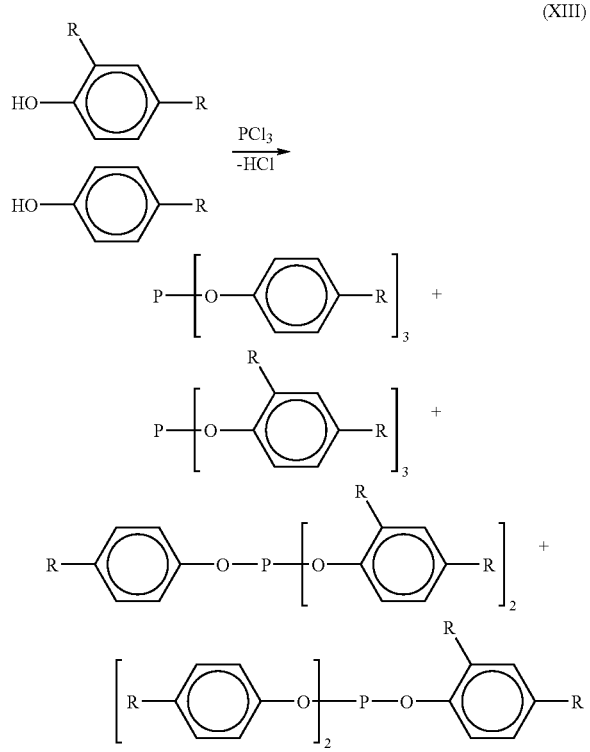

(XIII)

wherein R is independently $R_4$, $R_5$, and $R_6$ as defined above. Note that a minor amount of other alkylated phenolics, e.g., ortho-substituted monoalkylated phenolics, may be included as an additional reactant in the above reaction scheme and would form additional derivative phosphites, but these additional reactants and products have been omitted from Reaction (XIII) for clarity.

Stabilizing Composition

As discussed above, a stabilizing amount or effective amount of the phosphite compositions of the invention may be used as a secondary antioxidant for various types of polymers. As used herein, by "stabilizing amount" and an "effective amount" it is meant when the polymer composition containing the phosphites of the invention shows improved stability in any of its physical or color properties in comparison to an analogous polymer composition which does not include a phosphite composition of the invention. Examples of improved stability include improved stabilization against, for example, molecular weight degradation, color degradation, and the like from, for example, melt processing, weathering, and/or long term field exposure to air, heat, light, and/or other elements. In one example, improved stability is obtained in the form of one or both of lower initial color as measured by yellowing index (YI) and melt flow rate of the molten polymer or additional resistance to weathering, as measured, for example, by initial yellowing index, or by resistance to yellowing and change in color, when compared to a composition without the stabilizer additive.

The additives and stabilizers described herein are preferably present in an amount effective to improve composition stability. When one of the aforementioned phosphite compositions, e.g., butylaryl phosphite compositions, is utilized, the composition is generally present in an amount from about 0.001 to about 5 wt. %, e.g., from about 0.0025 to about 2 wt. % or from about 0.005 to about 1 wt. %, based on the total weight of the resin including the weight of the phosphite composition and any other stabilizers or additives. The phosphite compositions of this invention stabilize resins especially during high temperature processing with relatively little change in melt index and/or color, even after multiple extrusions.

The invention further relates to a stabilized thermoplastic polymeric resin composition, comprising a base polymer resin (polymeric resin) and any of the aforementioned phosphite compositions of the invention. The polymer resin may be a polymer such as a polyolefin, and the liquid phosphite composition may be used with a costabilizer, for example, hindered phenolics, aromatic amines, hydroxylamines, alkylamine-N-oxides, lactones, and thioethers. Thus, the thermoplastic resins stabilized by the phosphite compositions of the present invention may optionally contain one or more additional stabilizers or mixtures of stabilizers selected from the group consisting of the phenolic antioxidants, hindered amine light stabilizers (HALS), the ultraviolet light absorbers, phosphites, phosphonites, alkaline metal salts of fatty acids, hydrotalcites, metal oxides, epoxydized soybean oils, the hydroxylamines, the tertiary amine oxides, lactones, thermal reaction products of tertiary amine oxides, and the thiosynergists.

In one embodiment, the polymeric compositions comprising the inventive phosphite compositions demonstrate low Yellowness Index ("YI") values, e.g., as compared to the YI values of similar polymeric compositions, e.g., similar components and an equivalent phosphite content, prepared utilizing TNPP as a stabilizer. In one embodiment, the inventive polymeric compositions demonstrate a YI value that is similar or less than, e.g., at least 5% less than, at least 10% less than, or at least 15% less than, that of the TNPP-stabilized polymeric compositions.

In one embodiment, the polymeric compositions comprising the inventive phosphite compositions demonstrate at least equivalent and often superior melt flow retention, as compared to the melt flow retention of similar polymeric compositions prepared utilizing TNPP as a stabilizer. In one embodiment, the inventive polymeric compositions demonstrate a melt flow retention that is similar or less than, e.g., at least 5% less than, at least 10% less than, or at least 15% less than, that of the TNPP-stabilized polymeric compositions.

In one embodiment, the polymeric compositions comprising the inventive phosphite compositions demonstrate at least equivalent and often superior gas fading values, as compared to the gas fading values of similar polymeric compositions prepared utilizing TNPP as a stabilizer. In one embodiment, the inventive polymeric compositions demonstrate a gas value that is similar or less than, e.g., at least 5% less than, at least 10% less than, or at least 15% less than, that of the TNPP-stabilized polymeric compositions.

Thus, the inventive phosphites, clearly demonstrate the ability to stabilize polymeric compositions as effectively or more effectively than TNPP. The inventive phosphite compositions, however, do not present estrogenicity concerns.

In one embodiment, the amount of each component in the stabilizing composition, based on the total weight percent of the polymer or polymeric resin, is shown in Table 3.

TABLE 3

| Component | Range | Preferred Range |
|---|---|---|
| Liquid phosphite compositions | 0.001–5.0 wt % | 0.005–1.0 wt % |
| Primary antioxidant | 0–5.0 wt % | 0.005–2.0 wt % |
| UV or light stabilizers | 0–3.0 wt % | 0.001–2.0 wt % |
| Metal deactivators | 0–3.0 wt % | 0.001–2.0 wt % |
| Other secondary antioxidants | 0–3.0 wt % | 0.001–2.0 wt % |
| Peroxide scavengers | 0–3.0 wt % | 0.001–2.0 wt % |
| Polyamide stabilizers | 0–3.0 wt % | 0.001–2.0 wt % |
| Basic co-stabilizers | 0–3.0 wt % | 0.001–2.0 wt % |
| Nucleating and clarifying agents | 0–3.0 wt % | 0.001–2.0 wt % |
| Aminoxy propanoate | 0–3.0 wt % | 0.001–2.0 wt % |

Primary Antioxidants

The phosphite compositions of the invention or the resulting stabilized polymer compositions optionally also comprise primary antioxidants such as the following:

(i) Alkylated monophenols, for example: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2,6-bis(α-methylbenzyl)-4-methylphenol, 2-(α-methylcyclohexyl)-4,6-dimethylphenol, 2,6-dioctadecyl-4-methylphenol, 2,4,6,-tricyclohexyphenol, and 2,6-di-tert-butyl-4-methoxymethylphenol. Commercially available alkylated monophenols include Lowinox™ 624 and Naugard™ 431 made by Chemtura Corp. Other phenols are commercially available as BHEB from Nanjing Datang Chemical Co., Ltd.

(ii) Alkylated hydroquinones, for example, 2,6-di-tert-butyl-4-methoxyphenol, 2,5-di-tert-butyl-hydroquinone, 2,5-di-tert-amyl-hydroquinone, and 2,6-diphenyl-4octadecyloxyphenol. Commercially available alkylated hydroquinones include Lowinox AH25 made by Chemtura.

(iii) Hydroxylated thiodiphenyl ethers, for example, 2,2'-thio-bis-(6-tert-butyl-4-methylphenol), 2,2'-thio-bis-(4-octylphenol), 4,4'-thio-bis-(6-tert-butyl-3-methylphenol), and 4,4'-thio-bis-(6-tert-butyl-2-methyphenol). Commercially available hydroxylated thiodiphenyl ethers include Lowinox TMB6, and Lowinox TBP6 made by Chemtura.

(iv) Alkylidene-bisphenols, for example, 2,2'-methylene-bis-(6-tert-butyl-4-methylphenol), 2,2'-methylene-bis-(6-tert-butyl-4-ethylphenol), 2,2'-methylene-bis-(4-methyl-6-(α-methylcyclohexyl)phenol), 2,2'-methylene-bis-(4-methyl-6-cyclohexylphenol), 2,2'-methylene-bis-(6-nonyl-4-methylphenol), 2,2'-methylene-bis-(6-nonyl-4-methylphenol), 2,2'-methylene-bis-(6-(α-methylbenzyl)-4-nonylphenol), 2,2'-methylene-bis-(6-(alpha,alpha-dimethylbenzyl)-4-nonyl-phenol), 2,2'-methylene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenol)butane, 1,1-bis(2-methyl-4-hydroxy-5-tert-butylphenyl)butane, 2,2'-isobutylidene-bis(4,6-dimethylphenol), 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-dodecyl-mercaptobutane, ethyleneglycol-bis-(3,3,-bis-(3'-tert-butyl-4'-hydroxyphenyl)-butyrate)-di-(3-tert-butyl-4-hydroxy-5-methylphenyl)-dicyclopentadiene, and di-(2-(3'-tert-butyl-2'hydroxy-5'methyl-benzyl)-6-tert-butyl-4-methylphenyl)terephthalate. Commercially available alkylidene-bisphenols include Lowinox 22M46, Lowinox WSP, Lowinox 44B25, Naugard 536, Naugawhite™, and Lowinox 22IB46 made by Chemtura.

(v) Benzyl compounds, for example, 1,3,5-tris-(3,5-di-tert-butyl-4-hydroxybenzyl)-2,4,6-trimethylbenzene, bis-(3,5-di-tert-butyl-4-hydroxybenzyl)sulfide, isooctyl 3,5-di-tert-butyl-4-hydroxybenzyl-mercapto-acetate, bis-(4-tert-butyl-3-hydroxy-2,6-dimethylbenzyl)dithiol-terephthalate, 1,3,5-tris-(3,5-di-tert-butyl-4 hydroxybenzyl)isocyanurate, 1,3,5-tris-(4-tert-butyl-3-hydroxy-2,6-dimethylbenzyl) isocyanurate, 1,3,5-tris(4-t-butyl-3-hydroxy-2,6-dimethylbenzyl)-1,3,5-Triazine-2,4,6-(1H,3H,5H)-trione, dioctadecyl-3,5-di-tert-butyl-4-hydroxybenzyl-phosphonate, calcium salt of monoethyl 3,5-di-tert-butyl-4-hydroxybenzylphosphonate, 1,3,5-tris-(3,5-dicyclohexyl-4-hydroxybenzyl)isocyanurate. Commercially available benzyl compounds include Anox™ IC-14, Anox 330 and Lowinox 1790 made by Chemtura.

(vi) Acylaminophenols, for example, 4-hydroxylauric acid anilide, 4-hydroxy-stearic acid amilide, 2,4-bis-octylmercapto-6-(3,5-tert-butyl-4-hydroxyanilino)-s-triazine, and octyl-N-(3,5-di-tert-butyl-4-hydroxyphenyl)-carbamate.

(vii) Esters of beta-(3,5-di-tert-butyl-4-hydroxyphenol)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethylisocyanurate, thiodiethyleneglycol, di-hydroxyethyl oxalic acid diamide. Such phenols also include tetrakis [methylene {3,5-di-tert-butyl-4-hydroxycinnamate}]methane. Commercially available esters include Anox 20, Anox 1315, Lowinox GP45, Naugalube 38, Naugalube 531, Anox PP18, Naugard PS48 and Naugard XL-1 made by Chemtura.

(viii) Thio esters of beta-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, dihydroxyethyl oxalic acid diamide. Commercially available thio esters include Naugalube™ 15 and Anox 70 made by Chemtura.

(ix) Amides of beta-(3,5-di-tert-butyl-4-hydroxyphenol)-propionic acid for example, N,N'-di-(3,5-di-tert-butyl-4-hydroxyphenylpropionyl)-hexammethylen-diamine, N,N'-di-(3,5-di-tert-butyl-4-hydroxyphenylpropionyl) trimethylenediamine, N,N'-di-(3,5-di-tert-butyl-4-hydroxyphenylpropionyl)-hydrazine, N,N'-Hexamethylene bis[3-(3,5-di-t-butyl-4-hydroxyphenyl)propionamide, and 1,2-Bis(3,5-di-tert-butyl-4-hydroxyhydrocinnamoyl)hydrazine. Commercially available amides include Lowinox HD98 and Lowinox MD24 made by Chemtura.

(x) Other phenolic antioxidants include the following phenols. Polymeric phenols such as the reaction product of 4-methylphenol with dicyclopentadiene and isobutylene, commercially available as Lowinox CSTL; Chemtura. Alkylidene-poly-phenols, such as 1,3 tris(3-methyl-4-hydroxyl-5-t-butyl-phenyl)-butane (Lowinox CA22; Chemtura). Thio phenols such as 2,6-di-tert-butyl-4-(4,6-bis(octylthio)-1,3,5-triazin-2-ylamino) phenol (Irganox™ 565; Ciba), 4,6-bis(octylthiomethyl)-o-cresol (Irganox 1520; Ciba); 4,6-bis(dodecylthiomethyl)-o-cresol (Irganox 1726; Ciba). Hydroxyl amines, such as bis(octadecyl)hydroxylamine (Irgastab™ FS 042; Ciba). Ester phenols include bis[3,3-bis(4-hydroxy-3-tert-butyl phenyl)butanoic acid]glycol ester (Hostanox™ O3; Clariant Chemicals). Still other phenols include 2-[1-(2-hydroxy-3,5-di-tert-pentylphenyl)ethyl]-4,6-di-tert-pentylphenyl acrylate (Sumilizer GS; Sumitomo Chemical).

In one embodiment, the stabilizing composition comprises one phenolic selected from the group consisting of tetrakismethylene (3,5-di-t-butyl-4-hydroxylhydrocinnamate)

methane (Anox 20), 1,3,5-tris(3,5-di-t-butyl-4-hydroxybenzyl) isocyanurate (Anox IC-14), 1,3,5-tris(4-tert.-butyl-3-hydroxy-2,6-dimethylbenzyl)-1,3,5-triazine-2,4,6-(1H,3H,5H)-trione (Lowinox 1790), octyl-3-(3,5-di-t-butyl-4-hydroxyphenyl) propionate (Anox PP18), bis(octadecyl) hydroxylamine (Irgastab FS-042), 1,3,5-trimethyl-2,4,6-tris (3,5-di-tert-4-hydroxybenzyl)benzene (Anox 330), 2,6-bis (α-methylbenzyl)-4-methylphenol (Naugalube 431), 3,5-bis (1,1-dimethylethyl)-4-hydroxy-benzenepropanoic acid (Anox 1315), 2,6-di-t-butyl-4-ethyl-phenol (BHEB), and mixtures thereof, and the liquid phosphite composition defined herein.

The phosphite compositions and/or the resulting stabilized polymeric resin compositions optionally also comprise one or more UV absorbers and/or light stabilizers, such as the following:

(i) 2-(2'-hydroxyphenyl)-benzotriazoles, for example, the 5'-methyl-, 3'5'-di-tert-butyl-, 3'5'-di-tert-amyl-, 5'-tert-butyl-, 5'-tert-amyl-, 5'(1,1,3,3-tetramethylbutyl)-, 5-chloro-3', 5'-di-tert-butyl-, 5-chloro-3'-tert-butyl-5'methyl-, 3'-sec-butyl-5'tert-butyl-, 4'-octoxy, 3',5'-ditert-amyl-3',5'-bis-(α,α-dimethylbenzyl)-derivatives. Commercially available 2-(2'-hydroxyphenyl)-benzotriazoles include Lowilite™ 26, Lowilite 27, Lowilite 28, Lowilite 29, Lowilite 35, Lowilite 55, and Lowilite 234 made by Chemtura.

(ii) 2-Hydroxy-benzophenones, for example, the 4-hydroxy, 4-methoxy-, 4-octoxy, 4-decyloxy-, 4-dodecyloxy-, 4-benzyloxy-, 2,4-dihydroxy-, 4,2',4'-trihydroxy- and 2'-hydroxy-4,4'-dimethoxy-derivative. Exemplary 2-hydroxybenzophenones include 2-hydroxy-4-methoxybenzophenone, 2-hydroxy-4-ethoxybenzophenone, 2,4-dihydroxybenzophenone, and 2-hydroxy-4-propoxybenzophenone. Commercially available 2-(2'-hydroxyphenyl)-benzotriazoles include Lowilite 20, Lowilite 22, Lowilite 20S, and Lowilite 24 made by Chemtura.

(iii) Esters of substituted and unsubstituted benzoic acids for example, phenyl salicylate, 4-tert-butylphenyl-salicilate, octylphenyl salicylate, dibenzoylresorcinol, bis-(4-tert-butylbenzoyl)-resorcinol, benzoylresorcinol, 2,4-di-tert-butyl-phenyl-3,5-di-tert-butyl-4-hydroxybenzoate and hexadecyl-3,5-di-tert-butyl-4-hydroxybenzoate.

(iv) UV absorbers and light stabilizers may also comprise acrylates, for example, alpha-cyano-beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)-2-methyl-indoline.

(v) Nickel compounds are also suitable UV absorbers and light stabilizers. Exemplary nickel compounds include nickel complexes of 2,2'-thio-bis(4-(1,1,1,3-tetramethylbutyl)-phenol), such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-penyl undecyl ketoxime, nickel complexes of 1-phenyl-4-lauroyl-5-hydroxy-pyrazole, optionally with additional ligands. Commercially available nickel compounds include Lowilite Q84 (2,2'-Thiobis(4-tert-octyl-phenolato))-N-butylamine-Nichel(11) made by Chemtura.

(vi) Sterically hindered amines may be used as UV absorbers and light stabilizers. Sterically hindered amines, for example bis(2,2,6,6-tetramethylpiperidyl)-sebacate, bis-(1,2,2,6,6-pentamethylpiperidyl)-sebacate, n-butyl-3,5-di-tert-butyl-4-hydroxybenzyl malonic acid bis(1,2,2,6,6-pentamethylpiperidyl) ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylendiamine and 4-tert-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetra-carbonic acid, 1,1'(1,2-ethanediyl)-bis-(3,3,5,5-tetramethylpiperazinone). Such amines include hydroxylamines derived from hindered amines, such as di(1-hydroxy-2,2,6,6-tetramethylpiperidin-4-yl)sebacate: 1-hydroxy 2,2,6,6-tetramethyl-4-benzoxypiperidine; 1-hydroxy-2,2,6,6-tetramethyl-4-(3,5-di-tert-butyl-4-hydroxy hydrocinnamoyloxy)-piperidine; and N-(1-hydroxy-2,2,6,6-tetramethyl-piperidin-4-yl)-epsiloncaprolactam. Commercially available hindered amines include Lowilite 19, Lowilite 62, Lowilite 77, Lowilite 92 and Lowilite 94 made by Chemtura.

(vii) Oxalic acid diamides, for examples, 4,4'-dioctyloxy-oxanilide, 2,2'-di-octyloxy-5',5'-di-tert-butyloxanilide, 2,2'-di-dodecyloxy-5',5'di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'ethyl-5,4-di-tert-butyloxanilide and mixtures of o- and p-methoxy—as well as of o- and p-ethoxy-disubstituted oxanilides.

The polymer resins and phosphite compositions of the invention may also include one or more additional additives, including, for example, one or more of the following:

(i) Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydrophenylpropionyl)-hydrazine, salicyloylamino-1,2,4-triazole, bis-benzyliden-oxalic acid dihydrazide.

(ii) Additional secondary antioxidants such as additional phosphites and/or phosphonites, for example, triphenyl phosphite, diphenylalkyl phosphites, phenyldialkyl phosphites, tris(nonyl-phenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite tristearyl sorbitol triphosphite, bis(2,4-dicumylphenyl) pentaerythritol diphosphite, and tetrakis(2,4-di-tert-butylphenyl)4,4'-biphenylene diphosphonite. Commercially available secondary antioxidants include Naugalube TPP, Alkanox™ 240, Ultranox™ 626, Naugard P, Weston™ 399, Weston TNPP, Weston 430, Weston 618F, Weston 619F, Weston DPDP, Weston DPP, Weston PDDP, Weston PTP, Weston TDP, Weston TLP, Weston TPP, and Weston TLTTP (trilauryl trithio phosphite) made by Chemtura; Doverphos™ 4, Doverphos 4-HR, Doverphos 4-HR Plus, Doverphos HiPure 4, and Doverphos S-9228 made by Dover Chemical; and Hostanox PEPQ made by Clariant Chemicals.

(iii) Peroxide scavengers, for example, esters of betathio-dipropionic acid, for example the lauryl, stearyl, myristyl or tridecyl esters, mercaptobenzimidazole or the zinc salt of 2-mercaptobenzimidazole, zinc-dibutyldithiocaramate, dioctadecyldisulfide, pentaerythritoltetrakis-(beta-dodecylmercapto)-propionate.

(iv) Polyamide stabilizers, for example copper salts in combination with iodides and/or phosphorus compounds and salts of divalent manganese may also be included in the polymer resin and/or phosphite composition.

(v) Basic co-stabilizers, for example, melamine, polyvinylpyrrolidone, dicyandiamide, triallyl cyanurate, urea derivatives, hydrazine derivatives, amines, polyamides, polyurethanes, hydrotalcites, alkali metal salts and alkaline earth metal salts of higher fatty acids, for example, Ca stearate, calcium stearoyl lactate, calcium lactate, Zn stearate, Zn octoate, Mg stearate, Na ricinoleate and K palmirate, antimony pyrocatecholate or zinc pyrocatecholate. Commercially available co-stabilizers include Mark™ 6045, Mark 6045ACM, Mark 6055, Mark 6055ACM, Mark 6087ACM, Mark 6102, Mark CE 345, Mark CE 350, and Mark CE 387, made by Chemtura; and DHT-4A™ made by Kisuma Chemicals.

(vi) Nucleating and clarifying agents, for example, metal salts of 4-tert butylbenzoic acid, adipic acid, diphenylacetic acid, sorbitol and derivatives thereof, sodium benzoate, and benzoic acid.

(vii) Aminoxy propanoate derivatives such as methyl-3-(N,N-dibenzylaminoxy)propanoate; ethyl-3-(N,N-dibenzylaminoxy) propanonoate; 1,6-hexamethylene-bis(3-N,N-dibenzylaminoxy)proponoate); methyl-(2-(methyl)-3(N,N-dibenzylaminoxy)propanoate); octadecyl-3-(N,N-dibenzylaminoxy)propanoic acid; tetrakis (N,N-dibenzylaminoxy)ethyl carbonyl oxymethy)methane; octadecyl-3-(N,N-diethylaminoxy)-propanoate; 3-(N,N-dibenzylaminoxy)propanoic acid potassium salt; and 1,6-hexamethylene bis(3-(N-allyl-N-dodecyl aminoxy)propanoate).

(viii) Other additives, for example, plasticizers, lubricants, emulsifiers, pigments, optical brighteners, flameproofing agents, anti-static agents, blowing agents and thiosynergists such as dilaurythiodipropionate or distearylthiodipropionate.

Optionally in the polymer or polymeric resins there may also be from 5-50 wt %, e.g., 10-40 wt % or 15-30 wt % of fillers and reinforcing agents, for example, calcium carbonate, silicates, glass fibers, asbestos, talc, kaolin, mica, barium sulfate, metal oxides and hydroxides, carbon black and graphite.

The invention further pertains to a stabilized polymer, wherein one component comprises a liquid phosphite composition of the present invention and the other a polymer, such as a polyolefin, polyvinyl chloride, etc., or polymeric resins.

The polymer stabilized by such liquid phosphite compositions may be any polymer known in the art, such as polyolefin homopolymers and copolymers, thermoplastics, rubbers, polyesters, polyurethanes, polyalkylene terephthalates, polysulfones, polyimides, polyphenylene ethers, styrenic polymers and copolymers, polycarbonates, acrylic polymers, polyamides, polyacetals, halide-containing polymers, and biodegradable polymers. Mixtures of different polymers, such as polyphenylene ether/styrenic resin blends, polyvinyl chloride/ABS or other impact modified polymers, such as methacrylonitrile and α-methylstyrene containing ABS, and polyester/ABS or polycarbonate/ABS and polyester plus some other impact modifier may also be used. Such polymers are available commercially or may be made by means well known in the art. However, the stabilizer compositions of the invention are particularly useful in thermoplastic polymers, such as polyolefins, polycarbonates, polyesters, polyphenylene ethers and styrenic polymers, due to the extreme temperatures at which thermoplastic polymers are often processed and/or used.

The polymers used in combination with liquid phosphite compositions of the present invention are produced using a variety of polymerization processes including solution, high-pressure, slurry and gas phase using various catalysts including Ziegler-Natta, single-site, metallocene or Phillips-type catalysts. Non-limiting polymers useful with the liquid phosphite compositions include ethylene based polymers such as linear low density polyethylene, elastomers, plastomers, high density polyethylene, substantially linear long chain branched polymers, and low density polyethylene; and propylene based polymers such as polypropylene polymers including atactic, isotactic, and syndiotactic polypropylene polymers, and propylene copolymers such as propylene random, block or impact copolymers.

The polymers, typically ethylene based polymers, have a density in the range of from 0.86 g/cc to 0.97 g/cc, preferably in the range of from 0.88 g/cc to 0.965 g/cc, more preferably in the range of from 0.900 g/cc to 0.96 g/cc, even more preferably in the range of from 0.905 g/cc to 0.95 g/cc, yet even more preferably in the range from 0.910 g/cc to 0.940 g/cc, and most preferably greater than 0.915 g/cc, preferably greater than 0.920 g/cc, and most preferably greater than 0.925 g/cc. The polymers produced by the process of the invention typically have a molecular weight distribution, a weight average molecular weight to number average molecular weight (Mw/Mn) of greater than 1.5 to about 15, particularly greater than 2 to about 10, more preferably greater than about 2.2 to less than about 8, even more preferably from about 2.2 to less than 5, and most preferably from 2.5 to 4. The ratio of Mw/Mn can be measured by gel permeation chromatography techniques well known in the art. The polymers of the present invention in one embodiment have a melt index (MI) or (I2) as measured by ASTM-D-1238-E in the range from 0.01 dg/min to 1000 dg/min, more preferably from about 0.01 dg/min to about 100 dg/min, even more preferably from about 0.1 dg/min to about 50 dg/min, and most preferably from about 0.1 dg/min to about 10 dg/min. The polymers of the invention in one embodiment have a melt index ratio (I21/I2) (I21 is measured by ASTM-D-1238-F) of from 10 to less than 25, more preferably from about 15 to less than 25. The polymers of the invention in a preferred embodiment have a melt index ratio (I21/I2) (I21 is measured by ASTM-D-1238-F) of from preferably greater than 25, more preferably greater than 30, even more preferably greater that 40, still even more preferably greater than 50 and most preferably greater than 65.

Polymers used with liquid phosphites compositions of the invention are useful in such forming operations as film, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, geomembranes, and pond liners. Molded articles include single and multi-layered constructions in the form of bottles, tanks, large hollow articles, rigid food containers and toys, etc. In addition to the above, the liquid phosphite compositions are used in various rubber based products such as tires, barriers and the like.

In one embodiment, the liquid phosphite compositions should be approved for use in polymers, preferably polyolefins, that are used in contact with beverages, foods and other human consumables.

Polymers of monoolefins and diolefins, for example polypropylene, polyisobutylene, polybutene-1, polymethylpentene-1, polyisoprene, or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example, mixtures of polypropylene with polyisobutylene, polypropylene with polyethylene (for example PP/HDPE, PP/LDPE) and mixtures of different types of polyethylene (for example LDPE/HDPE), may also be used. Also useful are copolymers of monoolefins and diolefins with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene, isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidene-norbornene; as well as mixtures of such copolymers and their mixtures with polymers mentioned above, for example polypropylene/ethylene propylene-copolymers, LDPE/EVA, LDPE/EAA, LLDPE/EVA, and LLDPE/EAA.

The olefin polymers may be produced by, for example, polymerization of olefins in the presence of Ziegler-Natta catalysts optionally on supports such as, for example, $MgCl_2$, chromium 20 salts and complexes thereof, silica, silica-alumina and the like. The olefin polymers may also be produced utilizing chromium catalysts or single site catalysts, e.g., metallocene catalysts such as, for example, cyclopentadiene complexes of metals such as Ti and Zr. As one skilled in the art would readily appreciate, the polyethylene polymers used herein, e.g., LLDPE, can contain various comonomers such as, for example, 1-butene, 1-hexene and 1-octene comonomers.

Polymers may also include styrenic polymers, such as polystyrene, poly-(p-methylstyrene), 5 poly-(α-methylstyrene), copolymers of styrene or α-methylstyrene with dienes or acrylic derivatives, such as, for example, styrene/butadiene (SBR), styrene/acrylonitrile, styrene/alkyl methacrylate, styrene/maleic anhydride, styrene/maleimide, styrene/butadiene/ethyl acrylate, styrene/acrylonitrile/methylacrylate, mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene (SBS), styrene/isoprene/styrene (SIS), styrene/ethylene/butylene/styrene or styrene/ethylene/propylene/styrene.

Styrenic polymers may additionally or alternatively include graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene and copolymers thereof; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene-propylene-diene terpolymers, styrene and acrylonitrile on polyacrylates or polymethacrylates, styrene and acrylonitrile on acrylate/butadiene copolymers, as well as mixtures thereof with the styrenic copolymers indicated above.

Suitable rubbers include both natural rubber and synthetic rubbers, and combinations thereof. Synthetic rubbers include, but are not limited to, for example, thermoplastic rubbers, ethylene/alpha-olefin/non-conjugated polyene (EPDM) rubbers, ethylene/alpha-olefin (EPR) rubbers, styrene/butadiene rubbers, acrylic rubbers, nitrile rubbers, polyisoprene, polybutadiene, polychloroprene, acrylonitrile/butadiene (NBR) rubbers, polychloroprene rubbers, polybutadiene rubbers, isobutylene-isoprene copolymers, etc. Thermoplastic rubbers include SIS, solution and emulsion SBS, etc.

Nitrile polymers are also useful in the polymer composition of the invention. These include homopolymers and copolymers of acrylonitrile and its analogs, such as polymethacrylonitrile, polyacrylonitrile, acrylonitrile/butadiene polymers, acrylonitrile/alkyl acrylate polymers, acrylonitrile/alkyl methacrylate/butadiene polymers, and various ABS compositions as referred to above in regard to styrenics.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be stabilized with the phosphite compositions of the present invention. These include polymers such as polychloroprene, epichlorohydrin homo- and copolymers, polyvinyl chloride, polyvinyl bromide, polyvinyl fluoride, polyvinylidene chloride, chlorinated polyethylene, chlorinated polypropylene, fluorinated polyvinylidene, brominated polyethylene, chlorinated rubber, vinyl chloride-vinyl acetate copolymers, vinyl chloride-ethylene copolymer, vinyl chloride-propylene copolymer, vinyl chloridestyrene copolymer, vinyl chloride-isobutylene copolymer, vinyl chloride-vinylidene chloride copolymer, vinyl chloride-styrene-maleic anhydride terpolymer, vinyl chloride-styrene-acrylonitrile copolymer, vinyl chloride-butadiene copolymer, vinyl chloride isoprene copolymer, vinyl chloride-chlorinated propylene copolymer, vinyl chloride-vinylidene chloride-vinyl acetate terpolymer, vinyl chloride-acrylic acid ester copolymers, vinyl chloride-maleic acid ester copolymers, vinyl chloride-methacrylic acid ester copolymers, vinyl chloride-acrylonitrile copolymer and internally plasticized polyvinyl chloride.

Other useful polymers include homopolymers and copolymers of cyclic ethers, such as polyalkylene glycols, polyethylene oxide, polypropylene oxide or copolymers thereof with bisglycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1,4dimethylol-cyclohexane terephthalate, poly2(2,2,4(4-hydroxyphenyl)-propane) terephthalate and polyhydroxybenzoates as well as block copolyetheresters derived from polyethers having' hydroxyl end groups.

Polyamides and copolyamides which are derived from bisamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylene bisamine and adipic acid; polyamides prepared from hexamethylene bisamine and isophthalic or/and terephthalic acid and optionally an elastomer as modifier, for example poly-2,4,4 trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols and polyamides or copolyamides modified with EPDM or ABS may be used.

In another embodiment, the polymer comprises a biodegradable polymer or compostable polymer. Biodegradable polymers are those in which the degradation results from the action of naturally occurring microorganisms, such as bacteria, fungi and algae. Compostable polymers undergoes degradation by biological processes during composting to yield $CO_2$, water, inorganic compounds and a biomass at a rate consistent with other compostable materials. Typically the biodegradable or compostable polymers are derived from plant sources and are synthetically produced. Examples of biodegradable or compostable polymers include poly(glycolic acid) (PGA), poly(lactic acid) (PLA), and co-polymers thereof. Biodegradable or compostable polymers may also be derived from a blend of starch of a plant and a conventional petroleum-based polymer. For example, the biodegradable polymer may be blended with a polyolefin.

Polyolefin, polyalkylene terephthalate, polyphenylene ether and styrenic polymers, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

In one embodiment, the liquid phosphite compositions are added to stabilize natural and synthetic waxes, such as n-paraffin waxes, chloroparaffins, α-olefin waxes, microcrystalline waxes, polyethylene waxes, amide waxes, and Fisher-Tropsch waxes. These waxes may be suitable for making candles.

The instant stabilizers may readily be incorporated into the polymer by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized compositions of the invention may optionally also contain from about 0.001 to about 5 wt. %, e.g., from about 0.0025 to about 2 wt. % or from about 0.05 to about 0.25 wt. %, of various conventional additives, such as those described previously, or mixtures thereof.

The stabilizers of this invention advantageously assist with the stabilization of polymer compositions especially in high temperature processing against changes in melt index and/or color, even though the polymer may undergo a number of extrusions. The stabilizers of the present invention may readily be incorporated into the polymer compositions by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer.

The compositions of the present invention can be prepared by a variety of methods, such as those involving intimate admixing of the ingredients with any additional materials desired in the formulation. Suitable procedures include solution blending and melt blending. Because of the availability of melt blending equipment in commercial polymer processing facilities, melt processing procedures are generally preferred. Examples of equipment used in such melt compounding methods include: co-rotating and counter-rotating extruders, single screw extruders, disc-pack processors and various other types of extrusion equipment. In some instances, the compounded material exits the extruder through small exit holes in a die and the resulting strands of molten resin are cooled by passing the strands through a water bath. The cooled strands can be chopped into small pellets for packaging and further handling.

All of the ingredients may be added initially to the processing system, or else certain additives may be pre-compounded with each other or with a portion of the polymer or polymeric resin to make a stabilizer concentrate. Moreover, it is also sometimes advantageous to employ at least one vent port to allow venting (either atmospheric or vacuum) of the melt. Those of ordinary skill in the art will be able to adjust blending times and temperatures, as well as component addition location and sequence, without undue additional experimentation.

While the stabilizers of this invention may be conveniently incorporated by conventional techniques into polymers before the fabrication thereof into shaped articles, it is also possible to apply the instant stabilizers by a topical application to the finished articles. Articles may comprise the instant stabilizer compounds and polymers and may be made into, for example, head lamp covers, roofing sheets, telephone covers, aircraft interiors, building interiors, computer and business machine housings, automotive parts, and home appliances. The articles may be made by extrusion, injection molding, roto-molding, compaction, and other methods. This may be particularly useful with fiber applications where the instant stabilizers are applied topically to the fibers, for example, by way of a spin finish during the melt spinning process.

Other Applications

The phosphite compositions of the invention may have uses in addition to polymer stabilization. For example, it may be desirable to react the phosphite composition to form a new derivative product, that may of additional uses. Transesterification processes, for example, such as those disclosed in Hechenbleikner et al., U.S. Pat. No. 3,056,823, which is incorporated herein by reference, may also be employed. Specifically, the process described by Hechenbleikner et al. involves transesterifying a triaryl phosphite with a monohydroxy hydrocarbon in the presence of a small but catalytically effective amount of a metal alcoholate or metal phenolate. To avoid contamination, the alcoholate of the particular alcohol to be transesterified is employed. Instead of employing a preformed alcoholate, the alcoholate can be formed in situ by adding the metal, e.g., sodium, potassium or lithium to the alcohol prior to adding the triaryl phosphite. The mono alcohol and triaryl phosphite are reacted in the mol ratio of three mols of the alcohol to one mol of the triaryl phosphite.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner.

EXAMPLES

The present invention will be further understood in view of the following non-limiting examples.

Preparation of Butylate Composition (Inventive)

16.8 g of Dowex DR 2030 was washed three times, each with 50 g of molten phenol. The used phenol was discarded between washes. After the final wash the Dowex DR 2030/phenol slurry was charged to a pre-heated (about 90° C.) jacketed vessel under nitrogen. Additional molten phenol was charged to the vessel such that the total amount used was 338.2 g (3.59 moles). The mixture was heated to about 90° C. and agitation was initiated. 244.0 g (4.35 moles) of 2-methylpropene (butene) was added over 3 hours at a uniform rate and below the surface of the phenol using a sintered frit. Once the addition was complete, the reaction was held at about 90° C. to allow for transalkylation. After 3 hours of transalkylation, the reaction mixture was allowed to settle and the butylated phenol was decanted from the Dowex. 567.5 g of crude butylated phenol was obtained. 435 g of the crude butylated phenol were charged to a vacuum fractional distillation unit. The un-alkylated phenol and any residual water were removed by vacuum distillation under a pressure of 26 in Hg at an internal temperature of 138° C. (vapor temperature of 60° C.). The un-alkylated phenol/water removal was considered complete when the water content was less than 50 ppm and the phenol content was less than 0.5%. The mass of the dried alkylate was 309.2 g. To separate any undesired impurities, e.g., 2,4,6-tri-tert-butylphenol, from the main fraction, which contains 4-tert-butylphenol and 2,4,-di-tert-butylphenol, the main fraction was then distilled under a vacuum at 26 in Hg at an internal temperature of 143° C. (vapor temperature of 128° C.) until an internal temperature of 145° C. (vapor temperature of 136° C.) was reached. The mass of the dried alkylate was 395.5 g.

Analysis of Butylated Phenol Alkylate (Inventive)

TABLE 4

| Gas Chromatograph ("GC") analysis | |
| --- | --- |
| phenol | 0.00% |
| 2-tert-butylphenol | 1.23% |
| 4-tert-butylphenol | 78.06% |
| 2,4-di-tert-butylphenol | 19.70% |
| 2,4,6-tri-tert-butylphenol | 0.00% |
| Impurities | 1.01% |
| | (no one impurity was present in amounts greater than 0.12%. |
| $H_2O$ Content | <50 ppm |

Preparation of Butylaryl Phosphite Composition (Inventive)

335 g (2.08 moles) of molten butylated phenol alkylate was charged to a pre-heated (about 90° C.) jacketed vessel under nitrogen. The alkylate was heated to pre-heated about 90° C. and agitation was initiated. 90.3 g of (0.66 moles) of phosphorus trichloride was added over 3 hours at a uniform rate and below the surface of the amylated phenol. During the addition of the phosphorus trichloride, the temperature was ramped at a uniform rate from about 90° C. to about 150° C. The resultant HCl off-gas was absorbed by a scrubbing unit. Once all the phosphorus trichloride had been added, the reaction mixture was held at 150° C. for 1 hour or until the HCl production had stopped. The reaction mixture was then heated from 150° C. to 200° C. over 1 hour. Once the reaction mixture had reached 200° C., the reaction was degassed by applying a water vacuum (60-80 mbar of pressure). The reaction mixture was degassed until the total chlorine content was less than 25 ppm. Once the total chlorine content had reached this level, the reaction was cooled to about 100° C. The mass of the crude reaction mixture was 346.0 g. The excess butylated phenol was removed (to less than 1% as measured by GC) by distillation under a pressure of 1 mbar up to an internal temperature of 253° C. (vapor temperature 130° C.). The mass of butylaryl phosphite produced was 318.2 g. The mass of the amylated phenol recovered after distillation was 27.7 g.

Additional butylated phenol compositions were prepared as indicated in Table 5. The phosphites were prepared by reacting phosphorus trichloride with a butylated phenol composition. The butylated phenol compositions were prepared as indicated above, or by preparing a binary composition of 4-tert-butylphenol and 2,4-di-tert-butylphenol.

TABLE 5

| Butylate Compositions | | | | |
| --- | --- | --- | --- | --- |
| | GC % | | | |
| Mixture | Phenol | 2-tert-butylphenol | 4-tert-butylphenol | 2,4-di-tert-butylphenol |
| Alkylate | | | | |
| 1 | 0.94 | 3.20 | 76.55 | 18.90 |
| 2 | 0 | 1.23 | 78.06 | 19.70 |
| 3 | 0.34 | 1.34 | 84.9 | 13.10 |
| 4 | 0 | 1.39 | 84.45 | 13.06 |
| Binary | | | | |
| 5 | 0 | 0 | 75.00 | 25.00 |
| 6 | 0 | 0 | 80.00 | 20.00 |
| 7 | 0 | 0 | 66.70 | 33.30 |

These butylate compositions were reacted with phosphorus trichloride to form phosphite compositions, having the viscosities shown in Table 6, wherein Mixtures 8-11 correspond to Mixtures 1-4 and Mixtures 12-14 correspond to Mixtures 5-7.

TABLE 6

| Butylaryl Phosphite compositions | | | | | |
| --- | --- | --- | --- | --- | --- |
| | Viscosity, cSt | | | | Stability |
| Mixture | 30° C. | 40° C. | 50° C. | 60° C. | |
| A* | 3,182 | 1,237 | — | 242 | — |
| B* | 3,678 | 1,295 | — | 258 | — |
| 8 | 12,797 | 2,240 | — | 233 | Y |
| 9 | 20,544 | 3,186 | — | 270 | Y |
| 10 | 9,629 | 1,719 | — | 196 | N |
| 11 | 7,481 | 3,198 | 812 | — | — |
| 12 | 45,292 | 4,757 | 1,123 | 405 | — |
| 13 | 15,925 | 4,140 | 949 | — | — |
| 14 | — | 10,486 | 1,853 | — | — |

*Compositions A and B are TNPP.

As shown in Table 6, compositions 8 and 9 demonstrate a composition of butylaryl phosphites that remains a liquid after three freeze/thaw cycles. Table 6 also shows that the butylaryl phosphite compositions of the invention have higher viscosities, but still maintain their stability. For example, Compositions 8 and 9 show viscosities of 12,797 cSt and 20,544 cSt, respectively, while remaining liquid after three freeze/thaw cycles.

In addition, the data presented in Tables 4 and 5 demonstrate the ability to control the viscosity of the phosphite composition by adjusting the composition of the butylate composition. Specifically, in the butylate compositions, the ratios of 4-tert-butylphenol to 2,4-di-tert-butylphenol can be adjusted, thus adjusting the composition of the resultant phosphite composition, to control the viscosity and stability of the resultant phosphite composition. In addition, the amount of residual phenolic in the butylate composition can also be adjusted to control the viscosity of the resultant phosphite composition.

Also, the inventive compositions are liquid compositions. The individual components of the compositions are expected to be solids. The fact that the inventive compositions are stable and liquid in form is clearly surprising and unexpected due to the expected solid nature of the individual components of the compositions. To the contrary, one of ordinary skill in the art would expect a composition of these butylaryl phosphites to be solid in form.

Comparison of Inventive Phosphite Compositions to TNPP

Polymeric compositions were prepared by combining various phosphite stabilizer compositions with a Linear Low Density Polyethylene ("LLDPE") resin, a zinc stearate acid scavenger ("ZnSt"), and an additional stabilizer, Anox PP18® from Chemtura Corporation. In each case, the phosphite stabilizer was added in an amount sufficient to achieve a pure phosphite content of 17 ppm. TNPP was added to the Reference composition and a butylphenyl phosphite composition of the invention was added to Composition 41. Table 7 shows the components of the polymeric compositions.

TABLE 7

Polymeric Compositions

|  | Reference | 41 |
|---|---|---|
| LLDPE | 99.89 | 99.901 |
| ZnSt | 0.05 | 0.05 |
| Anox PP18 | 0.02 | 0.02 |
| TNPP | 0.04 | — |
| Butylphenyl phosphite composition | — | 0.029 |

These polymeric compositions were tested for Melt Flow Index ("MFI"), Yellowing Index ("YI"), and Gas Fading ("GF").

TABLE 8

MFI Results

|  | Pass 0 | Pass 1 | Pass 3 | Pass 5 |
|---|---|---|---|---|
| | MFI at 2.16 kg during multiple passes at 230° C., g/10 min. | | | |
| Reference | 0.967 | 0.904 | 0.778 | 0.637 |
| Composition 41 | 0.958 | 0.928 | 0.738 | 0.631 |
| | MFI at 21.6 kg during multiple passes at 230° C., g/10 min | | | |
| Reference | 23.027 | 23.066 | 21.614 | 20.973 |
| Composition 41 | 23.192 | 22.915 | 21.952 | 20.676 |

MFI is a measurement of melt flow. High melt flow is preferred, thus, minimizing reduction of melt flow over multiple passes is desirable. As shown in Table 8, at 2.16 kg, the reference composition (with TNPP) showed a Pass 0 MFI of 0.967 g/10 min. and a Pass 5 MFI of 0.637 g/10 min., which is a difference of 0.330 g/10 min. Composition 41 showed a Pass 0 MFI of 0.958 g/10 min. and a Pass 5 MFI of 0.631 g/10 min., which is a difference of 0.327 g/10 min. At 21.6 kg, the reference composition showed a Pass 0 MFI of 23.027 g/10 min. and a Pass 5 MFI of 20.973 g/10 min., which is a difference of 2.054 g/10 min. Composition 41 showed a Pass 0 MFI of 23.192 g/10 min. and a Pass 5 MFI of 20.676 g/10 min., which is a difference of 2.516 g/10 min. Thus, the melt flow retention of Composition 41 was quite similar to that of the reference composition.

TABLE 9

YI Results

|  | YI during multiple passes at 230° C., g/10 min | | | |
|---|---|---|---|---|
|  | Pass 0 | Pass 1 | Pass 3 | Pass 5 |
| Reference | −1.249 | 0.600 | 0.718 | 1.203 |
| Composition 41 | −1.182 | 0.311 | 0.446 | 0.615 |

YI is a measurement of the degree of color of a polymeric composition. A low YI is desirable. As shown in Table 9, the YI values for Composition 41 are similar to or less than the YI values for the reference composition.

TABLE 10

GF Results

|  | GF, after hours of NO$_x$ exposure | | | | |
|---|---|---|---|---|---|
|  | 2 | 25 | 94 | 120 | 140 |
| Reference | 3.26 | 6.27 | 9.34 | 10.11 | 10.52 |
| Composition 41 | 2.24 | 5.31 | 8.19 | 9.12 | 9.87 |

GF is a measurement of the degree of color of a polymeric composition with exposure to NO$_x$ gas. Again, a low GF is desirable. As shown in Table 10, the GF values for Composition 41 are less than the GF values for the reference composition.

As stated above, the inventive phosphites, clearly demonstrate the ability to stabilize polymeric compositions as effectively or more effectively than TNPP. As noted above, however, the inventive phosphite compositions do not present estrogenicity concerns.

In view of the many changes and modifications that can be made without departing from principles underlying the invention, reference should be made to the appended claims for an understanding of the scope of the protection to be afforded the invention.

What is claimed is:

1. A phosphite composition consisting essentially of:
   from 0 to 3 weight percent based on the total weight of the composition of a tris(dibutylaryl) phosphite;
   from 35 to 75 weight percent based on the total weight of the composition of a tris(monobutylaryl) phosphite;
   from 5 to 15 weight percent based on the total weight of the composition of a bis(dibutylaryl)monobutylaryl phosphite; and
   from 21 to 47 weight percent based on the total weight of the composition of a bis(monobutylaryl)dibutylaryl phosphite,
   wherein the composition is a liquid at ambient conditions.

2. The composition of claim 1, wherein at least 90% of the butyl substituents are tert-butyl.

3. An additive composition comprising a phenol in an amount from 1 to 4 weight percent, based on the total weight of the composition and the phosphite composition of claim 1.

4. The composition of claim 1, wherein the ratio of monobutylaryl groups to dibutylaryl groups ranges from 7:1 to 1:1.

5. The composition of claim 1, wherein the phosphite composition comprises greater than 60 weight percent monobutylaryl moieties and greater than 5 weight percent dibutylaryl moieties.

6. The composition of claim 1, wherein the composition has a viscosity ranging from 500 cSt to 50,000 cSt at 30° C.

7. The composition of claim 1, wherein the composition has a viscosity greater than 7,000 cSt at 30° C.

8. The composition of claim 1, wherein the composition has phosphorus content of at least 4.0 mole percent.

9. An additive composition comprising the phosphite composition of claim 1, and at least one additional component selected from the group consisting of phenolic antioxidants, amine stabilizers, hindered amine light stabilizers, ultraviolet light absorbers, phosphonites, alkaline metal salts of fatty acids, hydrotalcites, metal oxides, epoxidized oils, epoxidized soybean oils, hydroxylamines, lactones, thermal reaction products of tertiary amine oxides, thiosynergists, and additional phosphites.

10. An additive composition comprising the phosphite composition of claim 1, and an amine selected from the group consisting of triethanolamine, triisopropanolamine, diethanolamine, diisopropanolamine, tetraisopropanolethylenediamine, alkyl alkanolamines, and dialkyl dialkanolamines.

11. The composition of claim 1, wherein the composition is substantially free of phenols.

12. A stabilized polymeric composition comprising:
A) a polymeric resin; and
B) a phosphite composition according to claim 1.

13. A phosphite composition according to claim 1 consisting essentially of:
from 0 to 3 weight percent based on the total weight of the composition of a tris(dibutylaryl) phosphite;
from 45 to 65 weight percent based on the total weight of the composition of a tris(monobutylaryl) phosphite;
from 5 to 15 weight percent based on the total weight of the composition of a bis(dibutylaryl)monobutylaryl phosphite; and
from 26 to 42 weight percent based on the total weight of the composition of a bis(monobutylaryl)dibutylaryl phosphite.

14. The composition of claim 13, wherein at least 90% of the butyl substituents are tert-butyl.

15. An additive composition comprising a phenol in an amount from 1 to 4 weight percent, based on the total weight of the composition and the phosphite composition of claim 13.

16. The composition of claim 13, wherein the ratio of monobutylaryl groups to dibutylaryl groups ranges from 7:1 to 1:1.

17. The composition of claim 13, wherein the phosphite composition comprises greater than 60 weight percent monobutylaryl moieties and greater than 5 weight percent dibutylaryl moieties.

18. An additive composition comprising the phosphite composition of claim 13, and at least one additional component selected from the group consisting of phenolic antioxidants, amine stabilizers, hindered amine light stabilizers, ultraviolet light absorbers, phosphonites, alkaline metal salts of fatty acids, hydrotalcites, metal oxides, epoxidized oils, epoxidized soybean oils, hydroxylamines, lactones, thermal reaction products of tertiary amine oxides, thiosynergists, and additional phosphites.

19. An additive composition comprising the phosphite composition of claim 13, and an amine selected from the group consisting of triethanolamine, triisopropanolamine, diethanolamine, diisopropanolamine, tetraisopropanolethylenediamine, alkyl alkanolamines, and dialkyl dialkanolamines.

20. A stabilized polymeric composition comprising:
A) a polymeric resin; and
B) a phosphite composition according to claim 13.

\* \* \* \* \*